United States Patent
Muir et al.

(10) Patent No.: US 10,786,471 B2
(45) Date of Patent: Sep. 29, 2020

(54) METHODS AND PRODUCTS RELATED TO GLUTAMINASE INHIBITORS

(71) Applicant: Massachusetts Institute of Technology, Cambridge, MA (US)

(72) Inventors: Alexander Muir, Cambridge, MA (US); Matthew Vander Heiden, Cambridge, MA (US); Laura Danai, Brighton, MA (US); Dan Yi Gui, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 25 days.

(21) Appl. No.: 15/890,220

(22) Filed: Feb. 6, 2018

(65) Prior Publication Data

US 2018/0221321 A1    Aug. 9, 2018

Related U.S. Application Data

(60) Provisional application No. 62/455,463, filed on Feb. 6, 2017.

(51) Int. Cl.

| | | |
|---|---|---|
| *A61K 31/198* | (2006.01) | |
| *A61K 31/554* | (2006.01) | |
| *A61K 9/00* | (2006.01) | |
| *A61K 31/225* | (2006.01) | |
| *A61K 45/06* | (2006.01) | |
| *A61K 31/277* | (2006.01) | |
| *A61K 31/7105* | (2006.01) | |
| *A61K 38/17* | (2006.01) | |
| *G01N 33/68* | (2006.01) | |
| *A61P 35/00* | (2006.01) | |
| *A61K 31/69* | (2006.01) | |
| *A61K 31/501* | (2006.01) | |
| *A61K 31/255* | (2006.01) | |
| *A61K 45/00* | (2006.01) | |

(52) U.S. Cl.
CPC .......... *A61K 31/198* (2013.01); *A61K 9/0053* (2013.01); *A61K 31/225* (2013.01); *A61K 31/255* (2013.01); *A61K 31/277* (2013.01); *A61K 31/501* (2013.01); *A61K 31/554* (2013.01); *A61K 31/69* (2013.01); *A61K 31/7105* (2013.01); *A61K 38/1709* (2013.01); *A61K 45/00* (2013.01); *A61K 45/06* (2013.01); *A61P 35/00* (2018.01); *G01N 33/6893* (2013.01); *G01N 2333/47* (2013.01)

(58) Field of Classification Search
None
See application file for complete search history.

(56) References Cited

U.S. PATENT DOCUMENTS

| | | |
|---|---|---|
| 2015/0175559 A1 | 6/2015 | Cook et al. |
| 2016/0058759 A1 | 3/2016 | Heffernan et al. |
| 2019/0218618 A1* | 7/2019 | Klijn .................... A61K 31/337 |

FOREIGN PATENT DOCUMENTS

WO    WO 2016/108195 A1    7/2016

OTHER PUBLICATIONS

Huang et al., Cancer Res vol. 65(16):7446-7454, Aug. 15, 2005.*
Song et al., Current Topics in Medicinal Chemistry vol. 18:1-12, 2018.*
International Preliminary Report on Patentability dated Aug. 15, 2019 for Application No. PCT/US2018/017101.
Romero et al., Keap1 loss promotes Kras-driven lung cancer and results in dependence on glutaminolysis. Nat Med. Nov. 2017;23(11):1362-1368. doi:10.1038/nm.4407. Epub Oct. 2, 2017.
Sayin et al., Activation of the NRF2 antioxidant program generates an imbalance in central carbon metabolism in cancer. Elife. Oct. 2, 2017;6. pii: e28083. doi: 10.7554/eLife.28083.
PCT/US2018/017101, Aug. 15, 2019, International Preliminary Report on Patentability.
[No Author Listed], SLC7A11 solute carrier family 7 member 11 [ Homo sapiens (human) ]. NCBI Gene. Apr. 5, 2020. 6 pages.
[No Author Listed], Q9UPY5 (XCT_HUMAN). UniProtKB. Feb. 26, 2020. 13 pages.
International Search Report and Written Opinion dated Apr. 30, 2018 for Application No. PCT/US2018/017101.
Deberardinis et al., Fundamental of cancer metabolism. Oncology. May 27, 2016;2:e1600200, 18 pages.
Huang et al., Cystine-glutamate transporter SLC7A11 in Cancer Chemosensitivity and Chemoresistance. Cancer Res. Aug. 15, 2005;65(16):7446-54.
Muir et al., Environmental cystine drives glutamine anaplerosis and sensitizes cancer cells to glutaminase inhibition. eLife. Aug. 15, 2017;6:e27713, 27 pages.
PCT/US2018/017101, Apr. 30, 2018, International Search Report and Written Opinion.

* cited by examiner

*Primary Examiner* — Sean McGarry
(74) *Attorney, Agent, or Firm* — Wolf, Greenfield & Sacks, P.C.

(57) ABSTRACT

The invention relates to methods and related compositions for enhancing cancer therapy and in particular glutaminase inhibitor therapy. The methods involve methods for identifying patients susceptible to glutaminase inhibitor therapy as well as sensitizing patients to glutaminase inhibitor therapy.

31 Claims, 13 Drawing Sheets

METHODS AND PRODUCTS RELATED TO GLUTAMINASE INHIBITORS

RELATED APPLICATIONS

This application claims the benefit under 35 U.S.C. § 119(e) of U.S. provisional application No. 62/455,463, filed Feb. 6, 2017, which is incorporated by reference herein in its entirety.

GOVERNMENT FUNDING

This invention was made with Government support under Grant No. R01 CA201276 awarded by the National Institutes of Health. The Government has certain rights in the invention.

BACKGROUND OF INVENTION

Cancer cells exhibit altered metabolism in comparison to their normal parent tissues. This is thought to support the biosynthetic demands of proliferating tumors. It is a long-standing observation that most cancer cell lines utilize glutamine beyond protein and nitrogen needs. This is essential for many cell lines to grow in vitro.

An interesting question is why cancer cells require glutamine if not for protein and as a nitrogen donor. For many cells, the carbon skeleton is used for TCA cycle anaplerosis, and contributes to the formation of metabolites cells need to grow. Glutamine can enter the TCA cycle, and glutaminase is an enzyme that many cells use to catalyze the first reaction in glutamine catabolism to provide anaplerotic TCA cycle carbon. Of note, aspartate may be one important product of glutamine anaplerosis, and aspartate levels drop dramatically with glutamine is withdrawn from lung cancer cells in culture. The addition of aspartate alone allows these cells to proliferate in the absence of glutamine. As many cancer cells require glutamine entry into the TCA cycle to proliferate in vitro, and this depends on glutaminase, this has led to the development of clinical glutaminase inhibitors.

SUMMARY OF THE INVENTION

In some aspects, the disclosure provides a method of treating a subject, by administering to a subject having cancer a glutaminase inhibitor and cystine in an effective amount to treat the subject.

In some embodiments, the glutaminase inhibitor and cystine are administered together in a single formulation or in separate formulations.

In some embodiments, the cystine is administered before the glutaminase inhibitor. In some embodiments, the cystine is L-cystine or L-cysteine.

In some embodiments, the cystine is administered to the subject as a cysteine formulation or as a cystine formulation.

In some embodiments, the cystine is administered in an amount to produce a 50-300 micromolar concentration in blood of the subject, or in an amount to produce a 100-150 micromolar concentration in blood of the subject.

In some embodiments an SLC7A11 inducer is further administered to the subject.

In some embodiments, the cystine is administered in an amount greater than 0.5 mmol/kg.

Some embodiments further comprise determining whether a cystine/glutamate transporter, SLC7A11, is expressed in a cancer cell of the subject, wherein if the SLC7A11 is expressed in the cancer cell, the cancer cell is sensitive to glutaminase inhibitor therapy.

In some embodiments, the subject has low levels or no expression of SLC7A11, or the subject has high levels of SLC7A11.

In some aspects, the disclosure provides a method for enhancing a glutaminase inhibitor therapy in a subject, comprising administering to a subject receiving glutaminase inhibitor therapy cystine in an effective amount to sensitize the subject to the glutaminase inhibitor therapy.

In some embodiments, the cystine is administered in an amount to produce a 100-150 micromolar concentration in blood of the subject.

In some embodiments, the cystine is administered in an amount greater than 0.5 mmol/kg.

Some embodiments further comprise determining whether a cystine/glutamate transporter, SLC7A11, is expressed in a cancer cell of the subject, wherein if the SLC7A11 is expressed in the cancer cell, the cancer cell is sensitive to glutaminase inhibitor therapy.

In some embodiments, the cystine is L-cystine or L-cysteine.

In some aspects, the disclosure provides a method for enhancing a glutaminase inhibitor therapy in a subject, comprising administering to a subject receiving glutaminase inhibitor therapy a SLC7A11 inducer in an effective amount to induce expression of SLC7A11 in a cancer cell of the subject, thereby sensitizing the subject to the glutaminase inhibitor therapy.

In some embodiments, the SLC7A11 inducer is a small molecule Nrf2 activator, or KI-696, or dimethyl fumarate, or CDDO-Me, or AI-3, or an miRNA, or VEDA-1209, or a nucleic acid encoding SLC7A11.

Some embodiments further comprise administering cystine or cysteine to the subject.

Some embodiments further comprise determining whether SLC7A11 is expressed in a cancer cell of the subject, wherein if the SLC7A11 is expressed in the cancer cell, the cancer cell is sensitive to glutaminase inhibitor therapy.

In some aspects, the disclosure provides a method for detecting the presence or absence of a cystine/glutamate transporter in a cancer cell, comprising: obtaining a cancer cell from a human subject; and detecting whether a cystine/glutamate transporter, SLC7A11, is expressed in the cancer cell, wherein if the SLC7A11 is expressed in the cancer cell, the cancer cell is sensitive to glutaminase inhibitor therapy.

In some embodiments, the expression level of SLC7A11 is determined using PET imaging.

In some embodiments, the PET imaging is performed with a PET reagent, $^{18}F$-propyl-glutamate.

Some embodiments further comprise administering to the subject cystine or cysteine in an effective amount to sensitize the subject to glutaminase inhibitor therapy.

Some embodiments further comprise administering to the subject an SLC7A11 inducer in an effective amount to sensitize the subject to glutaminase inhibitor therapy.

In some embodiments of the methods described herein the cancer is non-small cell lung cancer (NSCLC).

In some aspects, the disclosure provides a composition comprising a glutaminase inhibitor and cystine in a pharmaceutically acceptable carrier.

In some embodiments, the cystine is L-cysteine or L-cystine.

In some aspects, the disclosure provides a kit comprising a container housing cystine in an oral dosage formulation, and instructions for administering the cystine to a subject receiving glutaminase inhibitor therapy.

In other aspects the invention is a composition of a glutaminase inhibitor and a SLC7A11 inducer in a pharmaceutically acceptable carrier. In some embodiments the composition further comprises cystine.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF DRAWINGS

The figures are illustrative only and are not required for enablement of the invention disclosed herein.

FIG. 1A is a diagram detailing the expected labeling patterns of glutamate, aspartate and TCA cycle intermediates from oxidative metabolism of $^{13}C_5$-glutamine. In FIG. 1B, the left panel shows enrichment of fully labeled glutamine (m+5) in the plasma of A549 tumor-bearing mice following a 6 h infusion of $^{13}C_5$-glutamine (n=5). The center and right panels show fractional labeling of glutamine (m+5), glutamate (m+5), α-ketoglutarate (m+5), fumarate (m+4), malate (m+4), aspartate (m+4) and citrate (m+4) in the A549 tumors following the 6 h $^{13}C_5$-glutamine infusion (n=5). FIG. 1C shows M+5 fractional labeling of glutamine, glutamate and α-ketoglutarate, and m+4 labeling of fumarate, malate, aspartate and citrate is shown for A549 cells cultured for 8 h in RPMI or adult bovine serum with $^{13}C_5$-glutamine added to ~33% enrichment (n=3). FIG. 1D shows the proliferation of A549 cells cultured in RPMI or adult bovine serum with vehicle (DMSO) or 1 μM CB-839 is shown (n=3). The calculation of cell proliferation rate is detailed in the Examples. For all parts of the figure, the values represent the mean and the error bars represent ±SEM.

FIG. 2A is a diagram detailing the generation of top 'Adult bovine serum→RPMI' and bottom 'RPMI→adult bovine serum'. For 'Adult bovine serum→RPMI', a small volume of RPMI was dialyzed repeatedly against large volumes of adult bovine serum using 3.5 kDa cutoff dialysis cassettes. This yields a medium where the >3.5 kDa fraction is 100% RPMI but the <3.5 kDa fraction is ~99% adult bovine serum. For 'RPMI→adult bovine serum', a small volume of adult bovine serum was repeatedly dialyzed against RPMI as above. FIG. 2B shows M+5 fractional labeling of glutamine, glutamate and α-ketoglutarate. M+4 labeling of fumarate, malate, aspartate and citrate is shown for A549 cells cultured for 8 h in 'Adult bovine serum→RPMI' and 'RPMI→adult bovine serum' with $^{13}C_5$-glutamine added to each media ~33% enrichment (n=3). FIG. 2C shows the proliferation of A549 cells cultured in RPMI, adult bovine serum, 'RPMI→adult bovine serum', 'Adult bovine serum→RPMI' with vehicle (DMSO) or 1 μM CB-839 is shown (n=3). For all panels, the values represent the mean and the error bars represent ±SEM.

FIG. 3A shows M+5 fractional labeling of glutamine, glutamate and α-ketoglutarate, and m+4 labeling of fumarate, malate, aspartate and citrate is shown for A549 cells cultured for 8 h in RPMI, adult bovine serum, adult bovine serum with RPMI nutrient levels, adult bovine serum with RPMI amino acid levels, and adult bovine serum with RPMI cystine added (208 μM). Each medium included $^{13}C_5$-glutamine added to ~33% enrichment (n=3). FIG. 3B shows the proliferation of A549 cells cultured in the same medias as in FIG. 3A, and RPMI containing only 10 μM cystine with vehicle (DMSO) or 1 μM CB-839 (n=3). For all parts of the figure, the values represent the mean and the error bars represent ±SEM.

FIG. 4A shows that xCT is a plasma membrane antiporter composed of two polypeptides, SLC7A11 and SLC3A2, that exchanges intracellular glutamate for extracellular cystine. Thus, xCT provides a link between the TCA cycle and cystine levels. FIG. 4B shows A549 cells that were infected with lentiviruses encoding a SLC7A11 targeting shRNA (TRCN0000288926) or a control shRNA targeting GFP. These cells were then infected with retroviruses either expressing shRNA-resistant SLC7A11 cDNA or empty vector (pLHCX). Shown is an immunoblot analysis of these modified cell lines. FIG. 4C shows the four cell lines from FIG. 4B, which were cultured for 8 h in adult bovine serum or adult bovine serum with 208 μM cystine. Each medium included $^{13}C_5$-glutamine added to ~33% enrichment (n=3). M+5 fractional labeling of α-ketoglutarate for each cell line in each condition was determined. Shown is the m+5 fractional label of α-ketoglutarate for a given cell line in adult bovine serum with 208 μM cystine minus the m+5 fractional label of α-ketoglutarate in adult bovine serum. This is termed the 'cystine induced contribution of glutamine to α-ketoglutarate'. FIG. 4D shows A549 cells that were infected with lentiviruses encoding SLC7A11 targeting shRNAs (TRCN0000288926, TRCN0000288865) or a control shRNA targeting GFP. Proliferation rates of these cells cultured in adult bovine serum or adult bovine serum with 208 μM cystine with vehicle (DMSO) or 1 μM CB-839 was determined (n=3). In FIG. 4E, multiple cell lines were cultured for 8 h in RPMI or RPMI (10 μM cystine). Each medium included $^{13}C_5$-glutamine added to ~33% enrichment (n=3). M+5 fractional labeling of α-ketoglutarate for each cell line in each condition was determined. Shown is the m+5 fractional label of α-ketoglutarate for a given cell line in RPMI minus the m+5 fractional label of α-ketoglutarate in RPMI (10 μM cystine). This is termed the 'cystine induced contribution of glutamine to α-ketoglutarate'. This value is plotted against SLC7A11 mRNA expression data obtained from the CCLE (Barretina et al., 2012). FIG. 4F shows dose response curves of CB-839 for panel of breast cancer cell lines cultured in RPMI was obtained from (Gross et al., 2014). These cells were grouped into 'resistant' cells where the IC50 was greater than the maximal CB-839 tested (1 μM) or sensitive cells where the IC50<1 μM. SLC7A11 mRNA expression data obtained from the CCLE (Barretina et al., 2012) is shown for each of these groups. Difference in SLC7A11 expression was tested by two-tailed unpaired t-test. FIG. 4G shows indicated cell lines that were infected with lentiviruses encoding SLC7A11 or empty vector. Shown is an immunoblot analysis of these modified cell lines. In FIG. 4H, cystine induced contribution of glutamine to α-ketoglutarate was determined as in FIG. 4E for the cell lines described in FIG. 4G. FIG. 4I shows proliferation rates for MCF7 cell lines from FIG. 4G grown in RPMI or RPMI (10 μM cystine) with vehicle (DMSO) or 1 μM CB-839 is shown. For all panels, values represent the mean and the error bars represent ±SEM.

In FIG. 5A, nu/nu mice were treated orally with 2.4 g/kg cystine and plasma from these animals was serially collected at the indicated time points. Cystine concentration of the plasma was determined by GC-MS. In FIG. 5B, A549 tumor-bearing mice were treated (n=4) or not (n=3) with oral cystine prior to bolus $^{13}C_5$-glutamine injection prior to harvesting the plasma and tumors. The left panel shows enrichment of m+5 glutamine and cystine concentration in the plasma of these animals. The right panel shows fractional labeling of glutamine (m+5), glutamate (m+5), α-ketoglutarate (m+5) in the A549 tumors following treatment and $^{13}C_5$-glutamine bolus injection. In FIG. 5C, intratumoral glutamate (m+5) and α-ketoglutarate (m+5) labeling from FIG. 5B were normalized to tumor glutamine (m+5).

FIG. 7A is a diagram detailing the generation of top 'Adult bovine serum→DMEM' and bottom 'DMEM→adult bovine serum'. For 'Adult bovine serum→DMEM', a small volume of DMEM was dialyzed repeatedly against large volumes of adult bovine serum using 3.5 kDa cutoff dialysis cassettes. This yields a medium where the >3.5 kDa fraction is 100% DMEM but the <3.5 kDa fraction is ~99% adult bovine serum. For 'DMEM→adult bovine serum', a small volume of adult bovine serum was repeatedly dialyzed against DMEM as above. FIG. 7B shows M+5 fractional labeling of glutamine, glutamate and α-ketoglutarate, and m+4 labeling of fumarate, malate, aspartate and citrate for A549 cells cultured for 8 h in DMEM, adult bovine serum and 'Adult bovine serum→DMEM' with $^{13}C_5$-glutamine added to each media ~33% enrichment (n=3). FIG. 7C shows the proliferation of A549 cells cultured in DMEM, adult bovine serum, 'DMEM→adult bovine serum', 'Adult bovine serum→DMEM' with vehicle (DMSO) or 1 μM CB-839 is shown (n=3). For all panels, the values represent the mean and the error bars represent ±SEM.

In FIG. 8A, A549 cells were cultured in adult bovine serum with DMEM nutrient levels, adult bovine serum with DMEM amino acid levels, and adult bovine serum with DMEM amino acid levels but without supplementation of the amino acids indicated in each column. For each medium, the proliferation rate for cells grown with vehicle (DMSO) or 1 μM CB-839 is shown (n=3). In FIG. 8B, A549 cells were cultured in adult bovine serum, adult bovine serum with DMEM amino acid levels, adult bovine serum with DMEM amino acids without serine, glycine, threonine or cystine supplemented, or the previous medium supplemented as indicated on the chart with DMEM levels of serine, glycine, threonine or cystine individually. For each medium, the proliferation rate for cells grown with vehicle (DMSO) or 1 μM CB-839 is shown (n=3). For all panels, the values represent the mean and the error bars represent ±SEM.

DESCRIPTION OF INVENTION

Figure 1A:
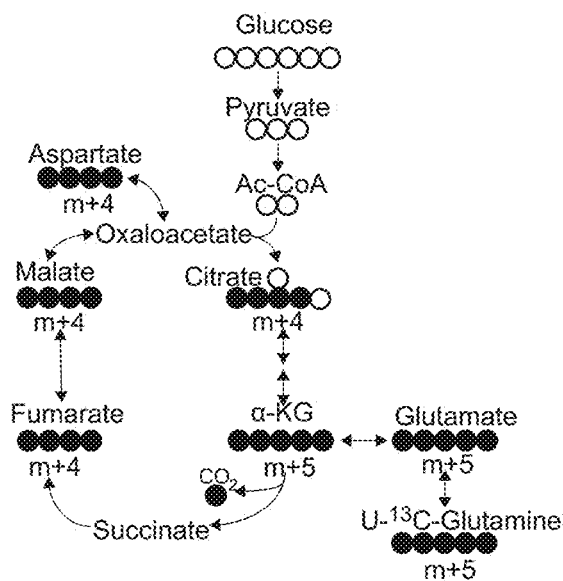
FIGS. 1A-1D show a human NSCLC model that exhibits decreased glutamine anaplerosis when growing in vivo and in bovine serum compared to RPMI.
Figure 1B:
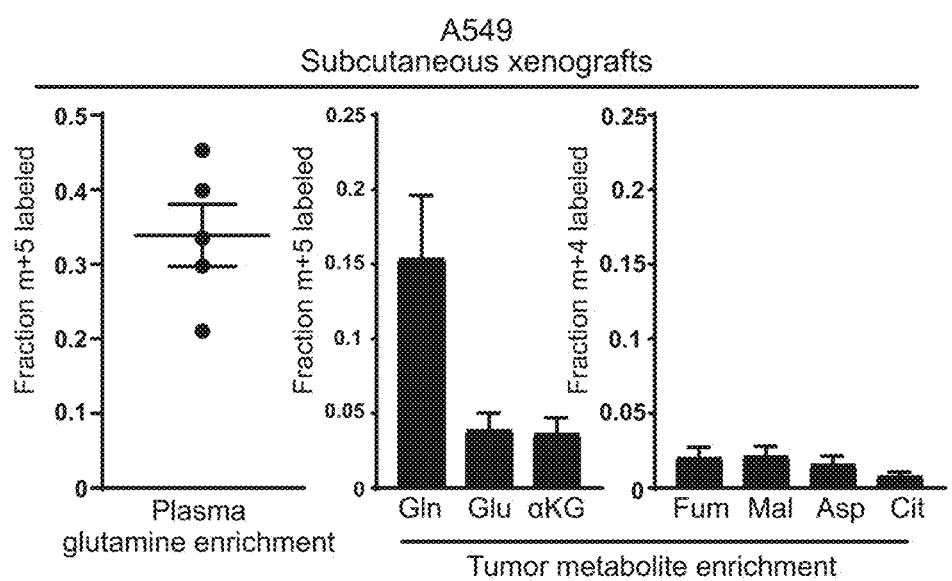
Figure 1C:
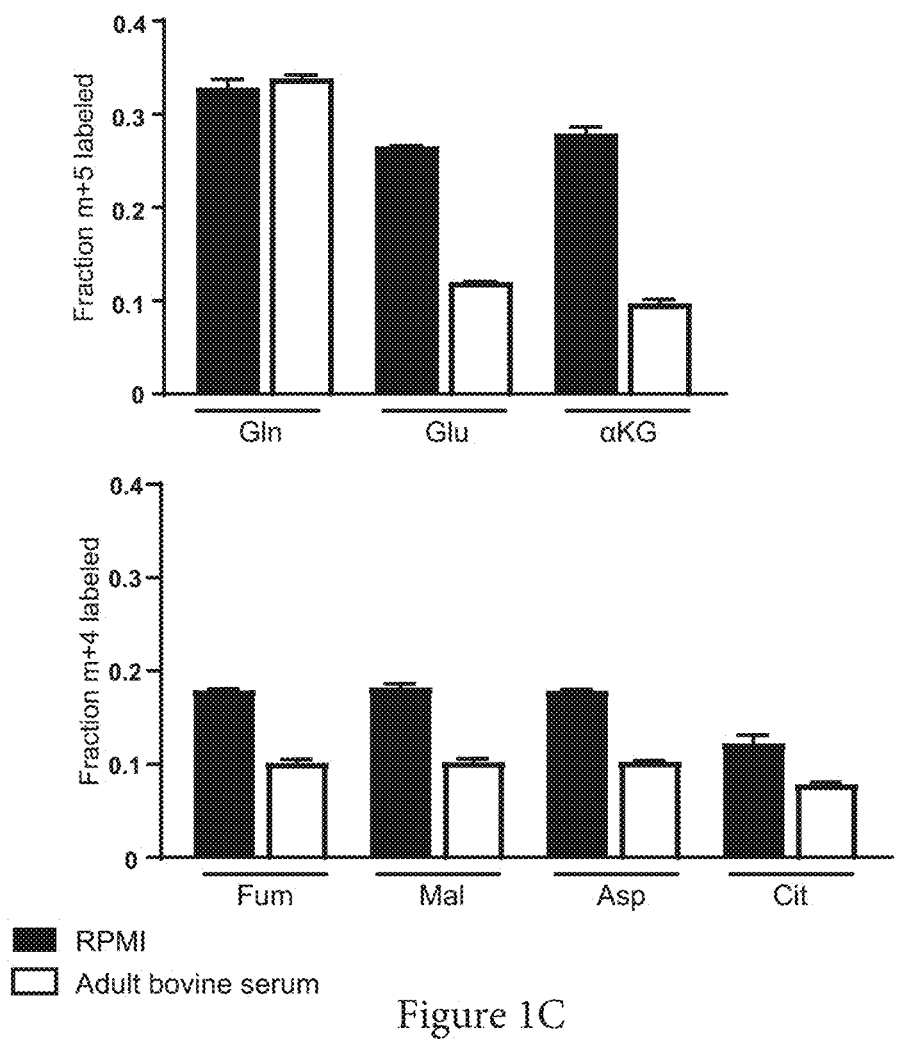
Figure 1D:
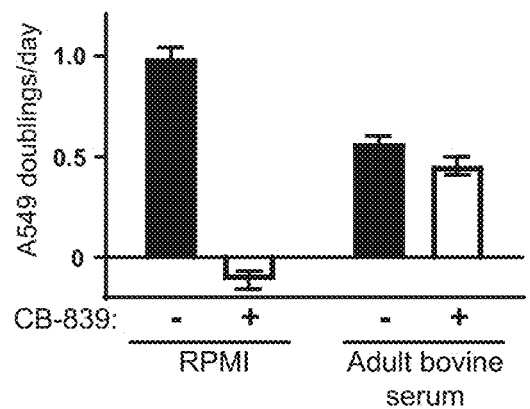
Figure 2A:
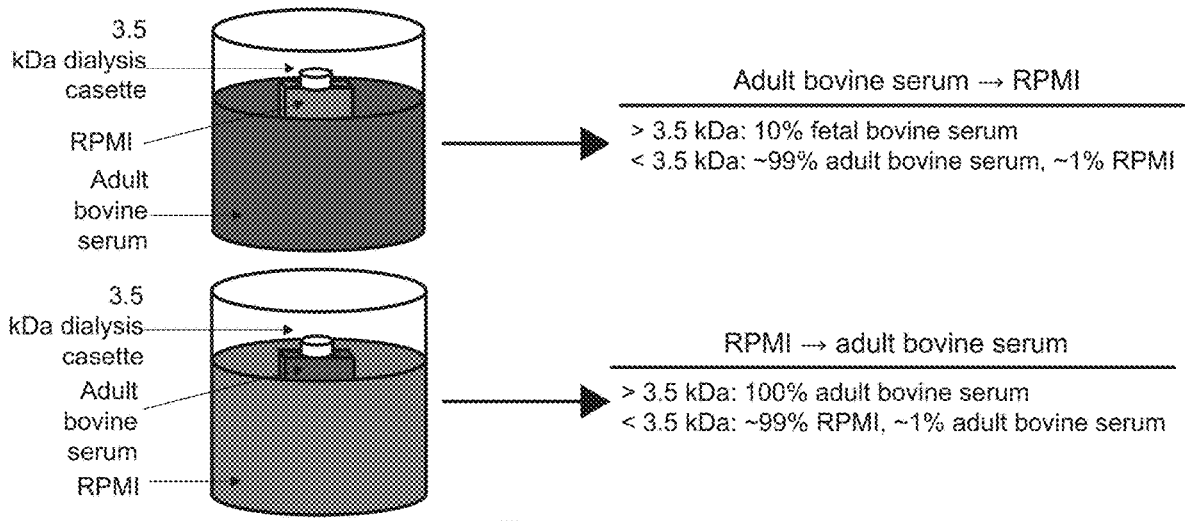
FIGS. 2A-2C show that the differences in the small molecule (<3.5 kDa) fraction between RPMI and adult bovine serum account for differences in glutamine anaplerosis and sensitivity to glutaminase inhibition.
Figure 2B:
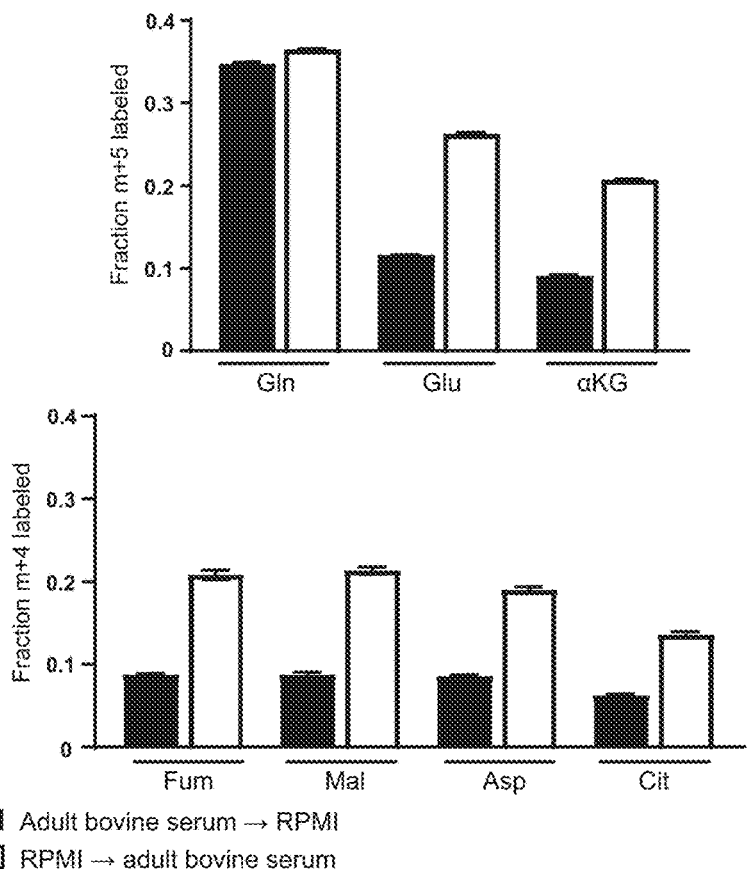
Figure 2C:
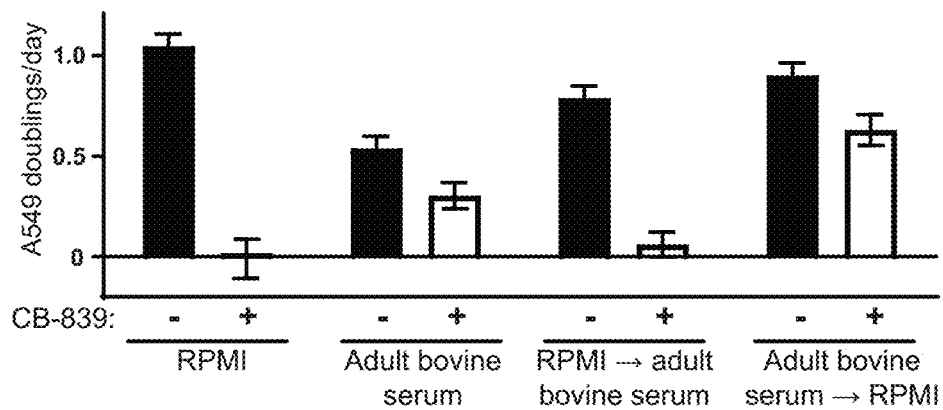
Figure 3A:
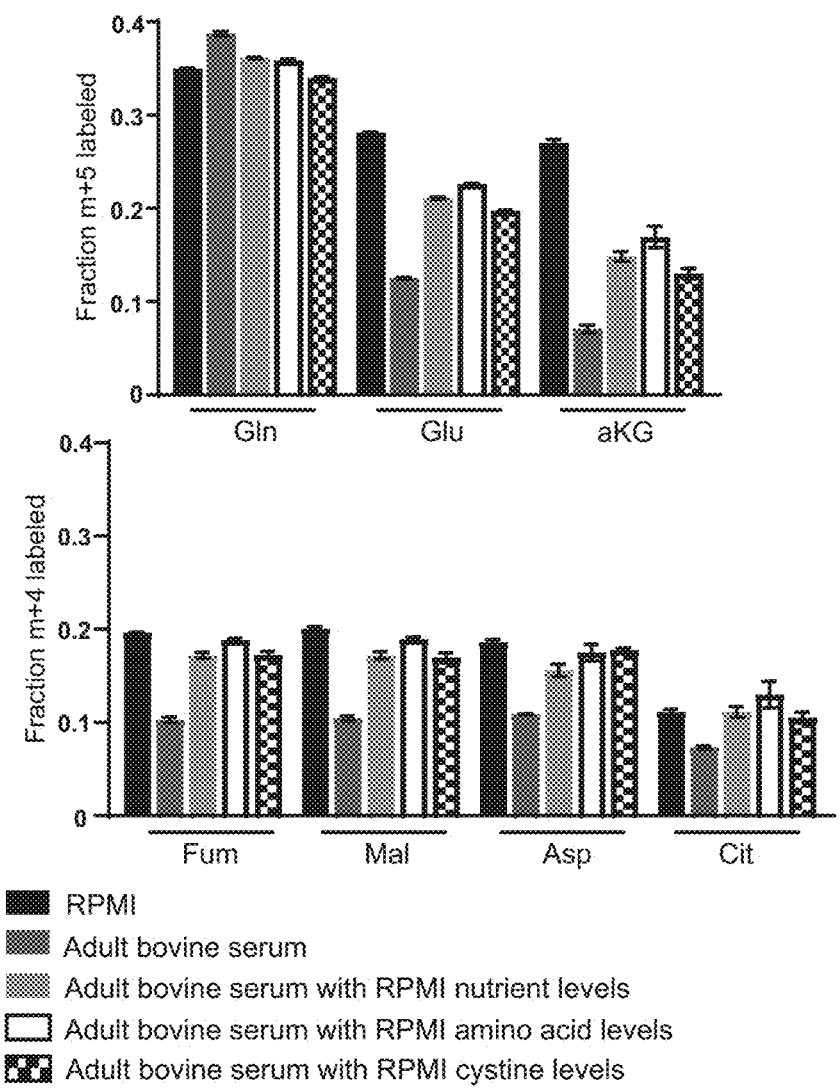
FIGS. 3A and 3B show that high levels of cystine enhance glutamine anaplerosis and potentiate the effects of the glutaminase inhibitor CB-839.
Figure 3B:
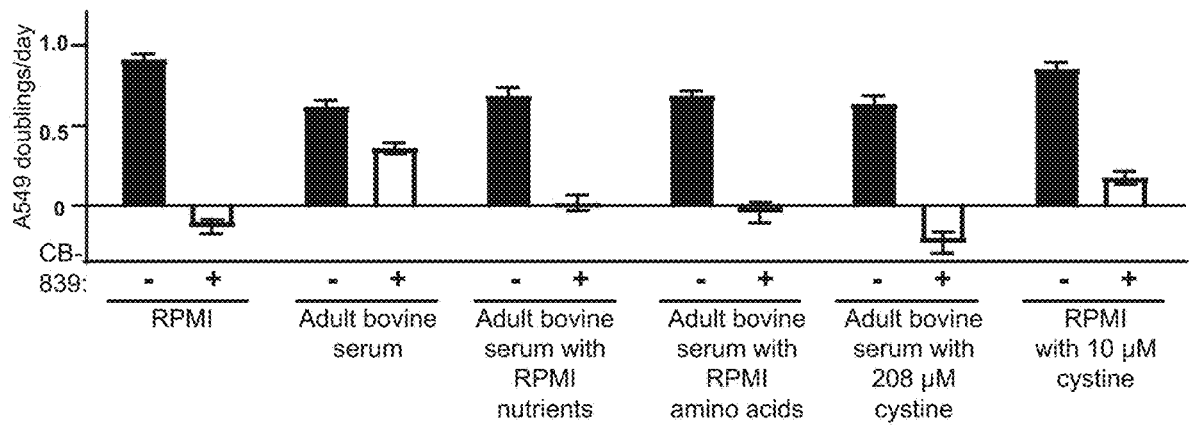
Figure 4A:
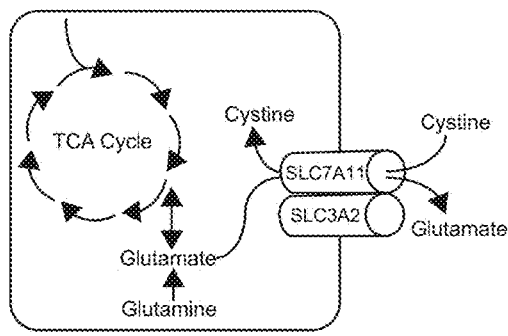
FIGS. 4A-4I show that the cystine/glutamate antiporter xCT/SLC7A11 is necessary and sufficient for cystine-induced glutamine anaplerosis and CB-839 sensitivity.
Figure 4B:
Figure 4C:
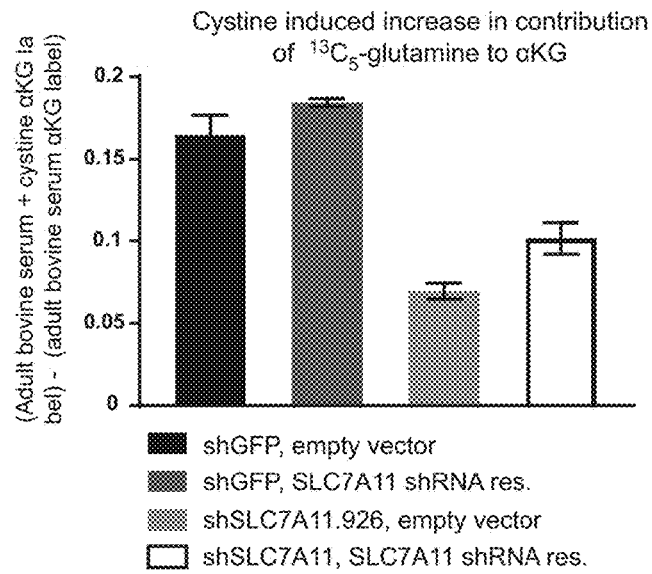
Figure 4D:
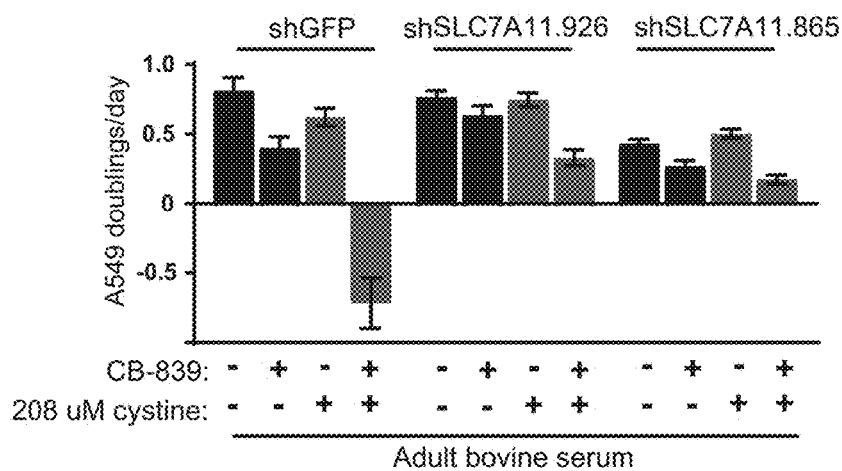
Figure 4E:
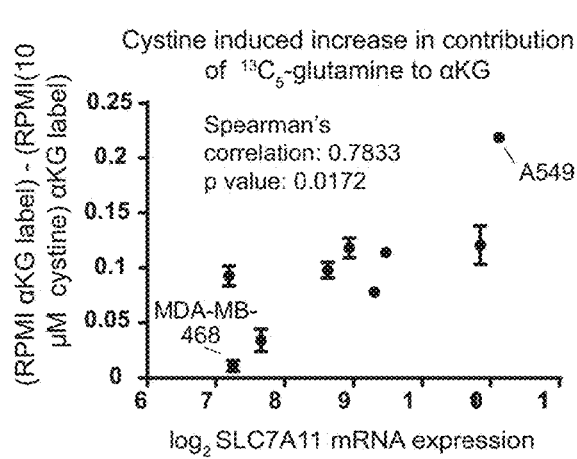
Figure 4F:
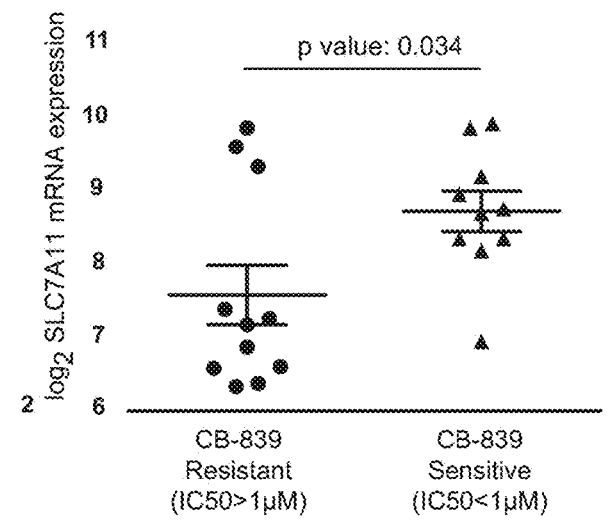
Figure 4G:
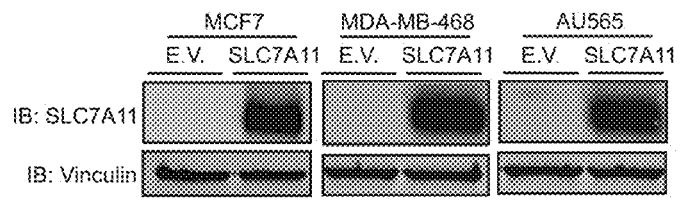
Figure 4H:
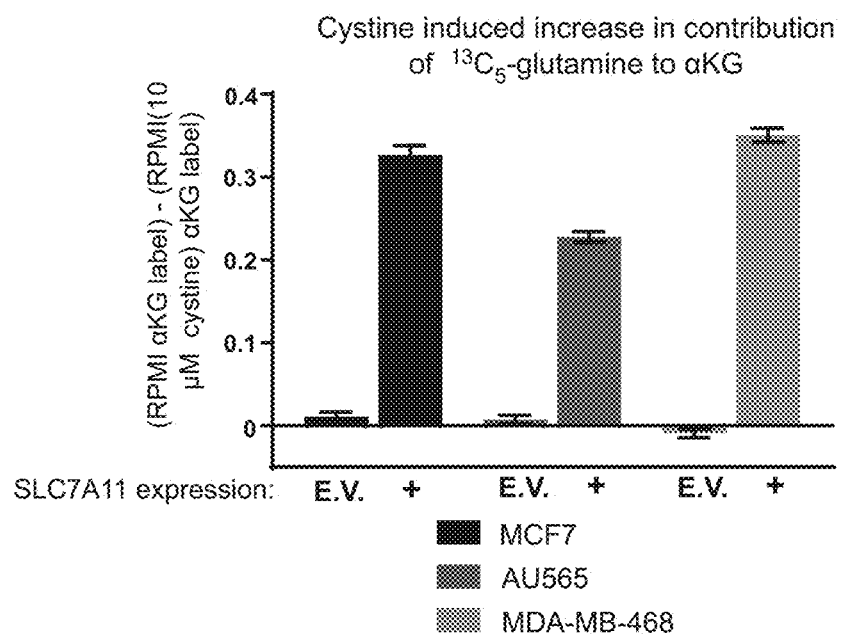
Figure 4I:
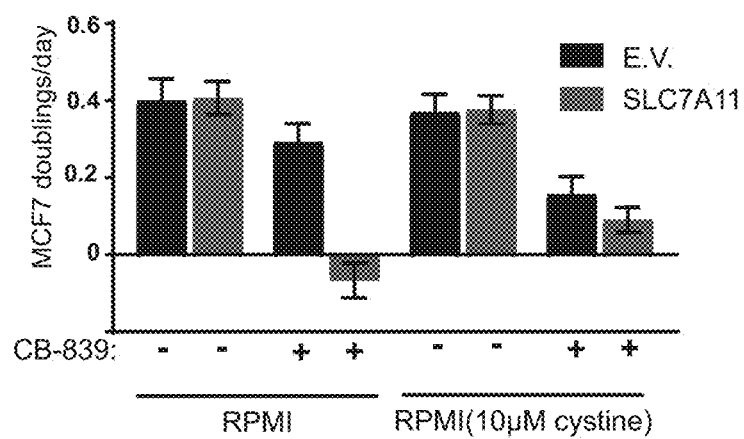
Figure 5A:
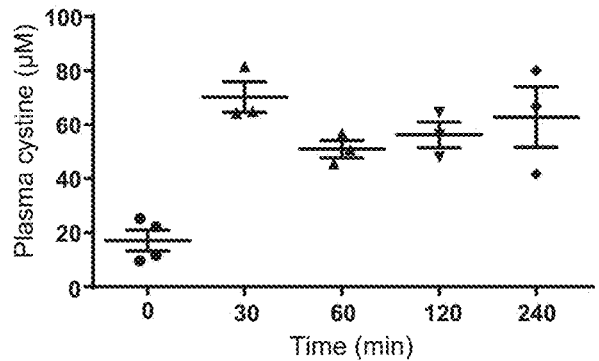
FIGS. 5A-5C show that raising cystine levels increases tumor glutamine anaplerosis in vivo.
Figure 5B:
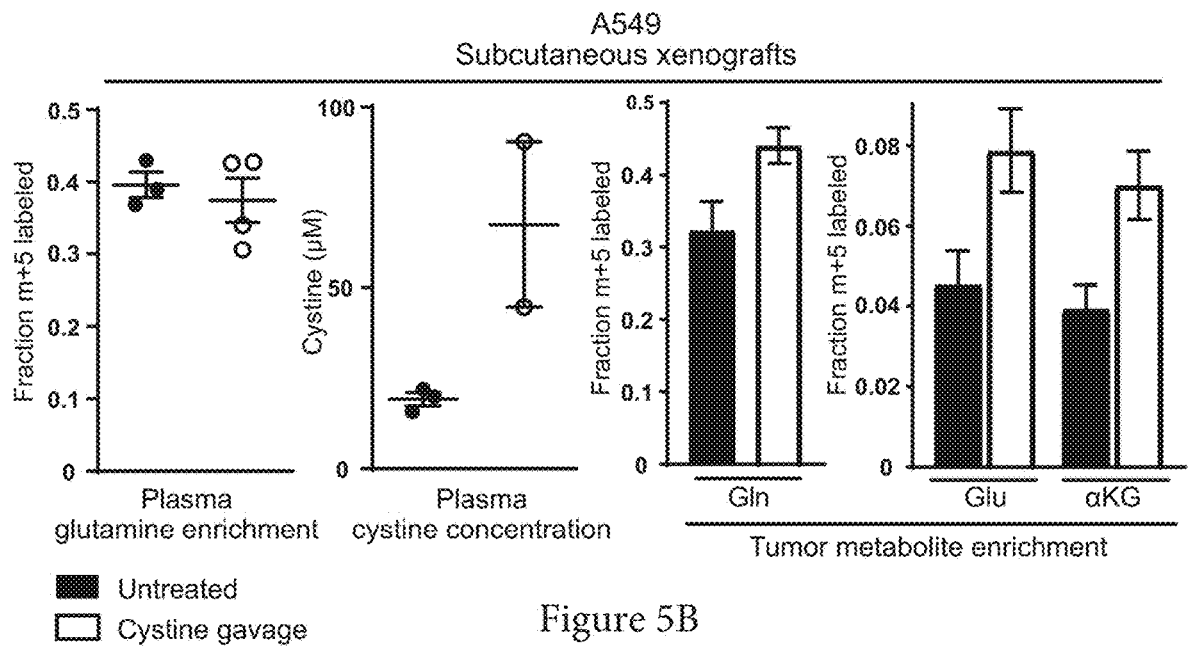
Figure 5C:
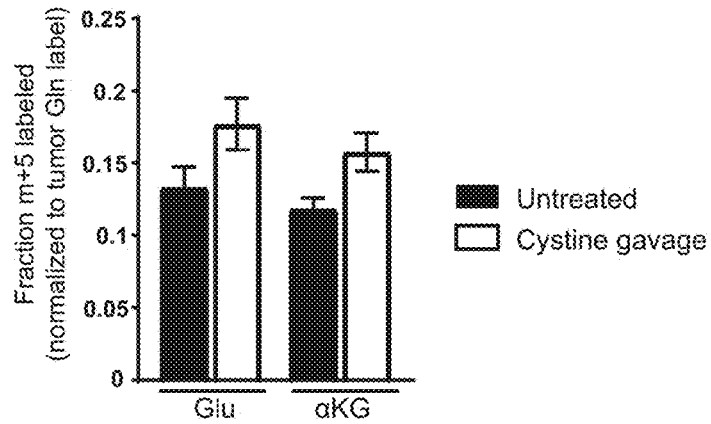
Figure 6:
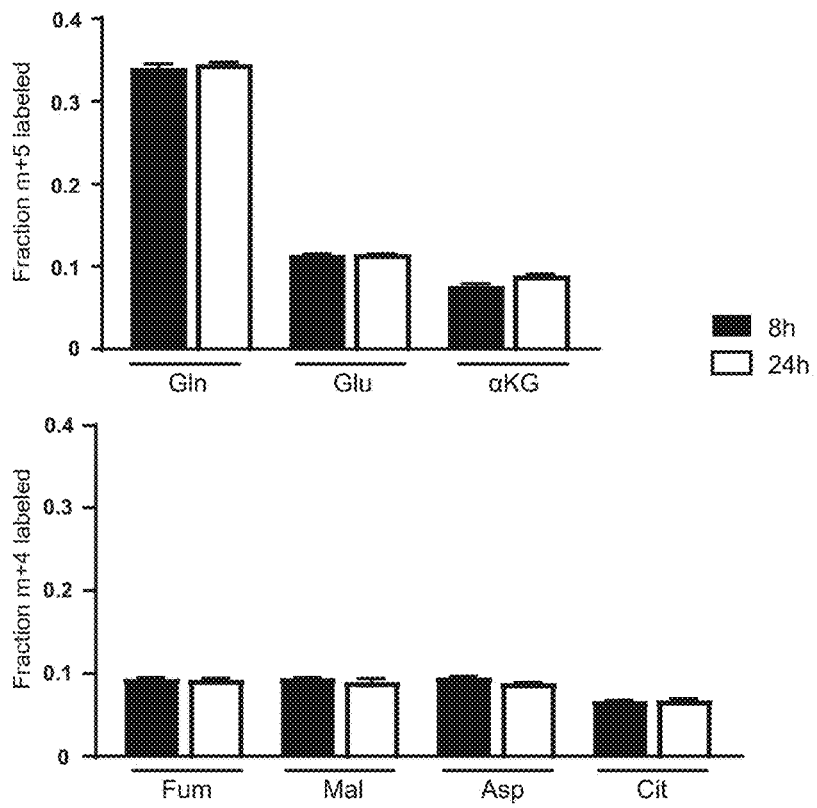
FIG. 6 shows that glutamine tracing reaches isotopic steady state by 8 hours. M+5 fractional labeling of glutamine, glutamate and α-ketoglutarate, and m+4 labeling of fumarate, malate, aspartate and citrate is shown for A549 cells cultured for 8 h or 24 h in adult bovine serum with $^{13}C_5$-glutamine added to ~33% enrichment (n=3). The values represent the mean and the error bars represent ±SEM.
Figure 7A:
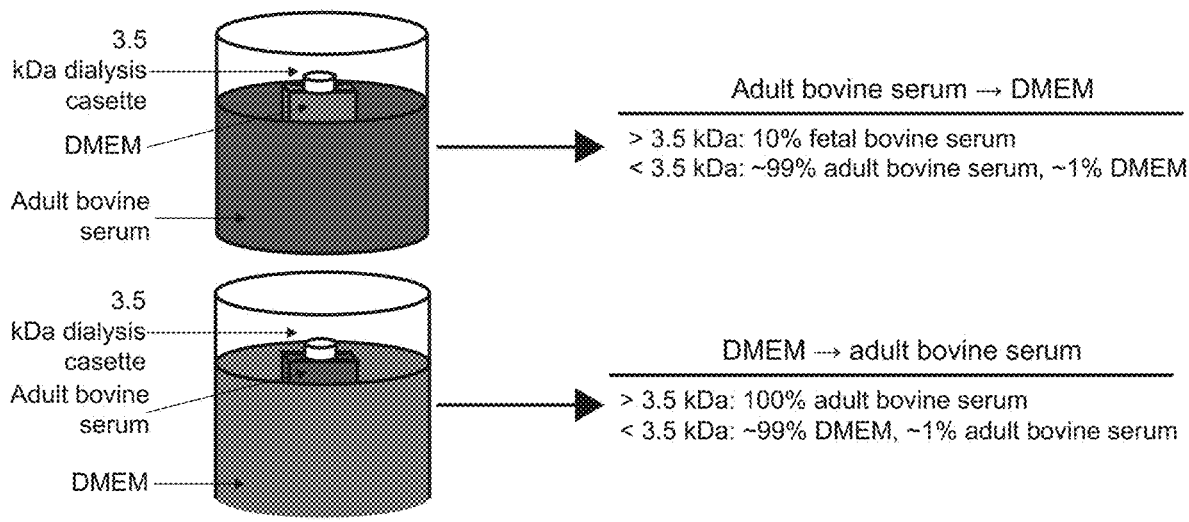
FIGS. 7A-7C shows that differences in the small molecule (<3.5 kDa) fraction between DMEM and adult bovine serum account for differences in glutamine anaplerosis and sensitivity to glutaminase inhibition.
Figure 7B:
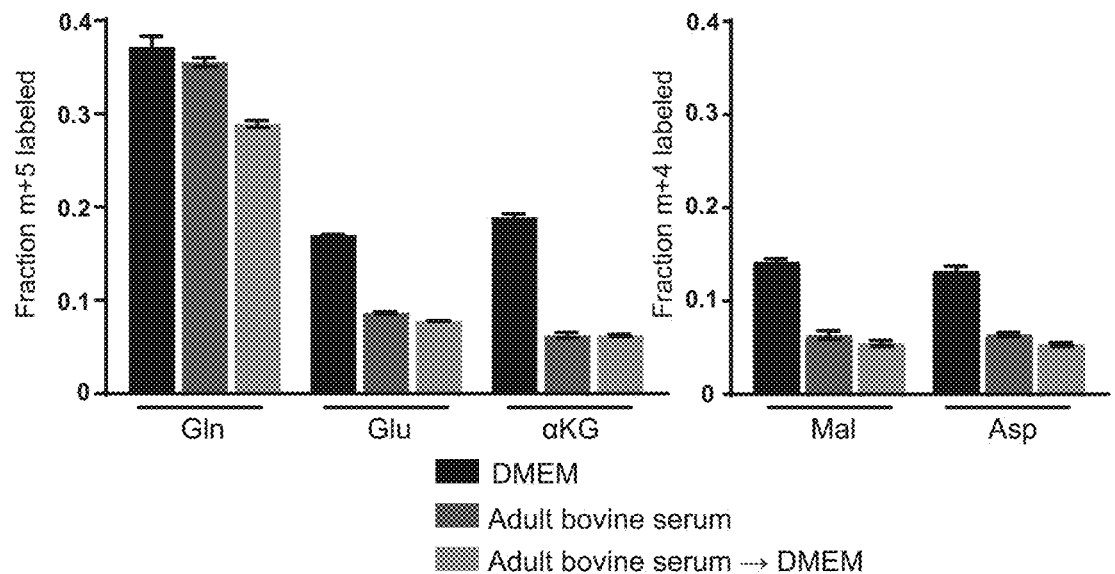
Figure 7C:
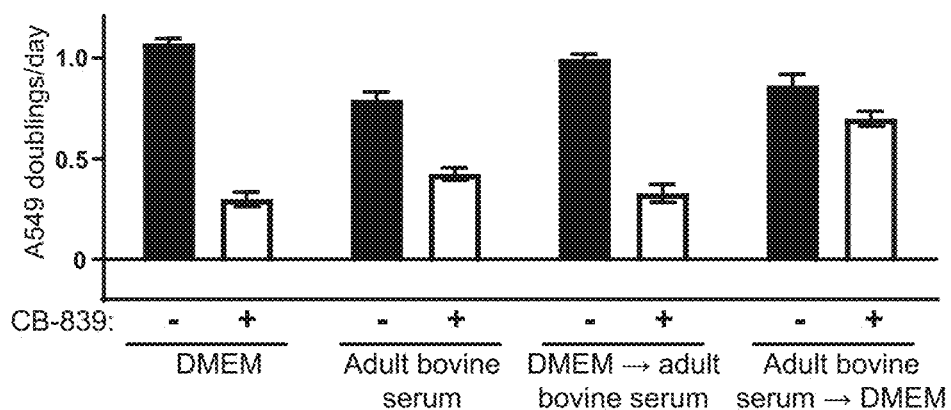
Figure 8A:
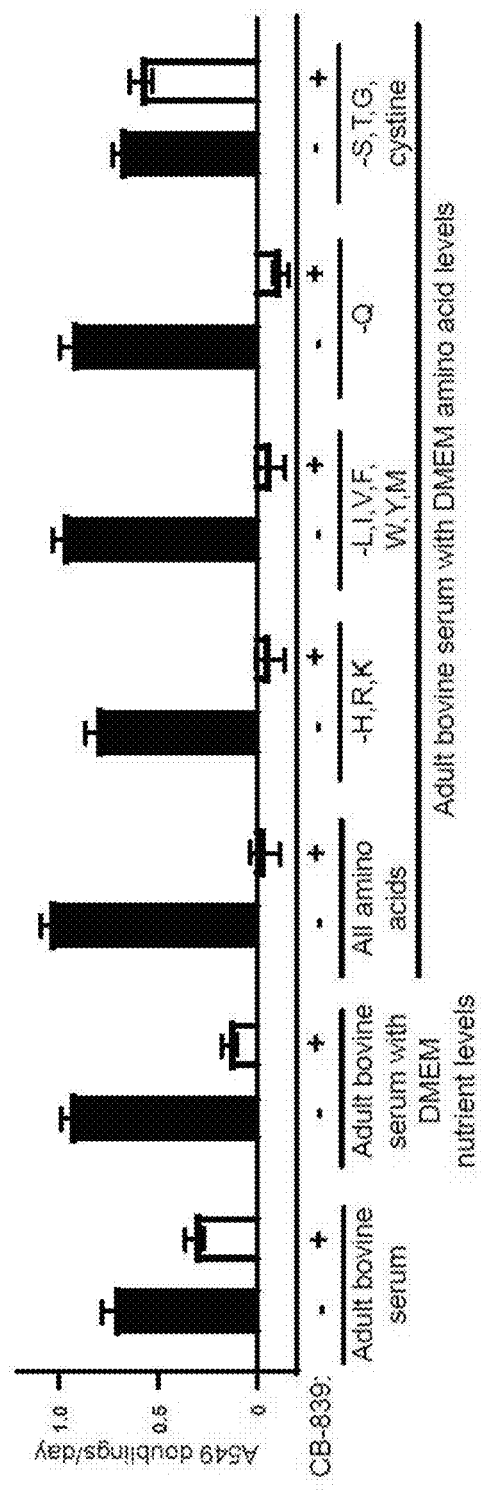
FIGS. 8A and 8B show the identification of cystine as the metabolite in DMEM/RPMI that potentiates the glutaminase inhibitor CB-839.
Figure 8B:
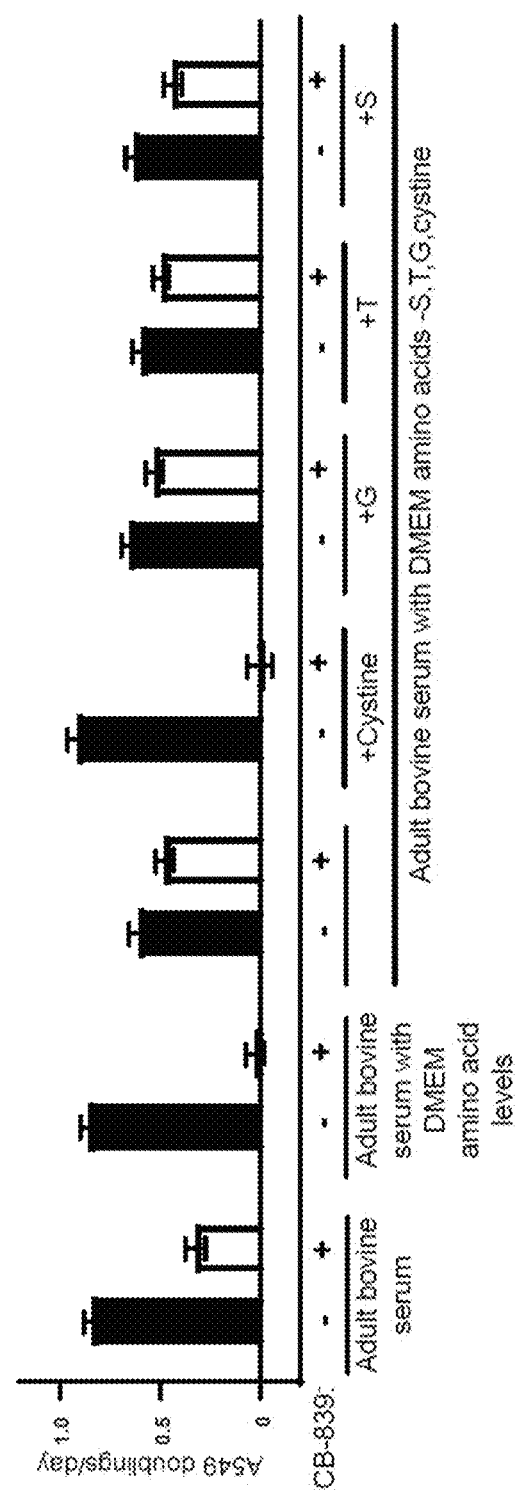
Figure 9A:
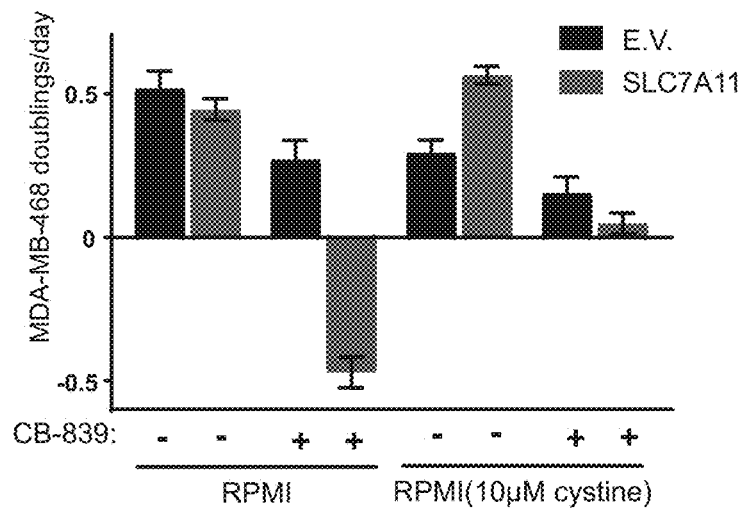
FIGS. 9A and 9B show that overexpression of xCT/SLC7A11 causes cystine-induced CB-839 sensitivity for MDA-MB-468 (FIG. 9A) and AU565 (FIG. 9B) breast cancer cell lines. Proliferation rates for MDA-MB-468 and AU565 cell lines overexpressing SLC7A11 or not (from FIG. 4G) in RPMI or RPMI (10 μM cystine) with vehicle (DMSO) or 1 μM CB-839 are shown. The values represent the mean and the error bars represent ±SEM.
Figure 9B:
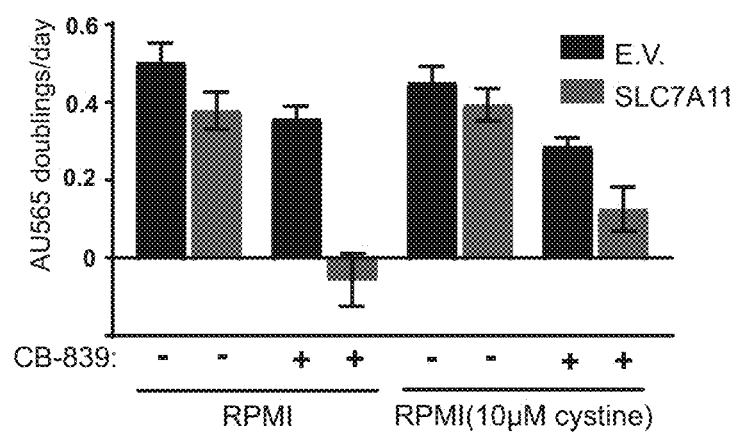
Figure 10:
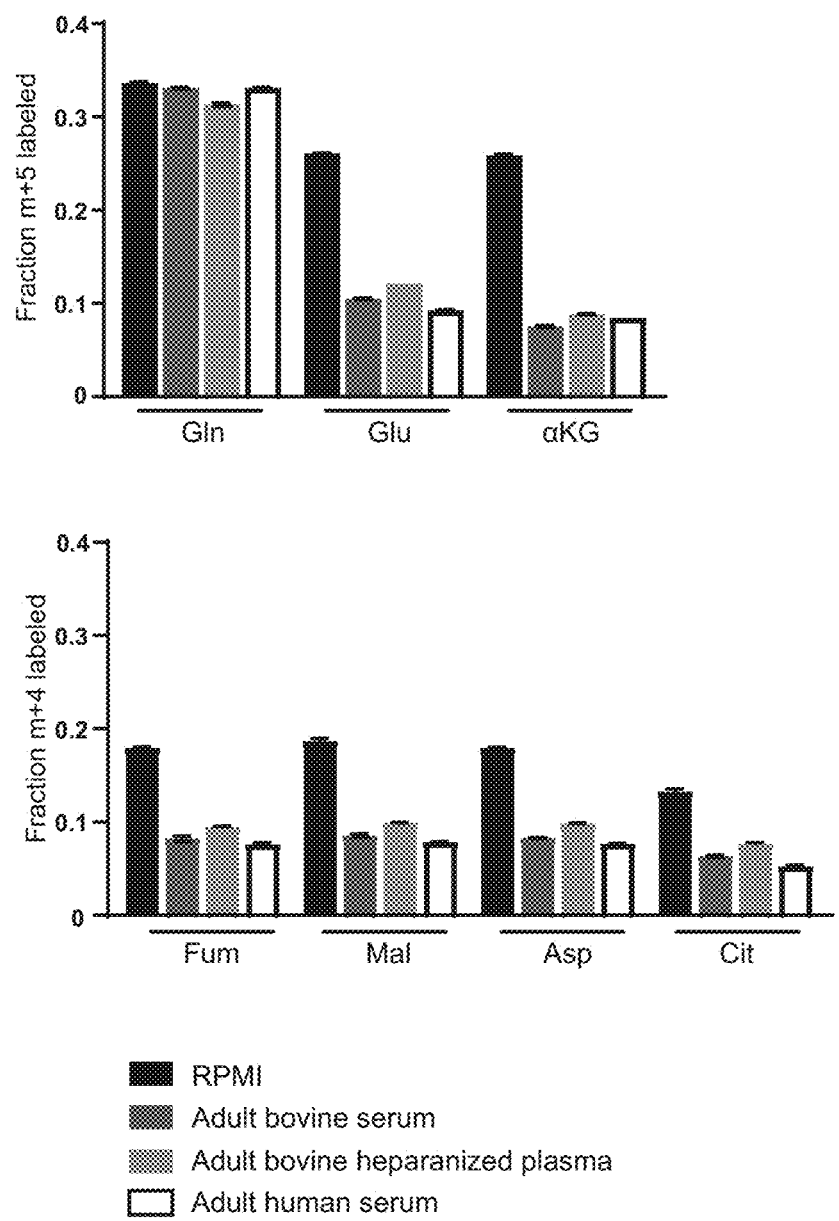
FIG. 10 shows that decreased glutamine anaplerosis is not unique to serum or bovine derived blood products. M+5 fractional labeling of glutamine, glutamate and α-ketoglutarate, and m+4 labeling of fumarate, malate, aspartate and citrate is shown for A549 cells cultured for 8 h in RPMI, adult bovine serum, adult heparinized plasma or adult human serum with $^{13}C_5$-glutamine added to ~33% enrichment (n=3). The values represent the mean and the error bars represent ±SEM.

A recurring problem with cancer therapy is inconsistent responses to the therapy in different patients. For instance one type of cancer therapy, glutaminase inhibitors, while quite effective in some patients, is not effective in other patients. Glutaminase inhibitors are used to interrupt glutamine anaplerosis in cancer cells. However not all cancers are sensitive to this therapy. Additionally, while a cancer cell may be sensitive to the therapy in vitro in many cases it may not be sensitive in vivo. In those case the patient will not response to the glutamine inhibitors.

It has been discovered according to the invention that an environmental difference between in vitro culture and in vivo suppresses glutamine anaplerosis, such that in tissue culture models this metabolic phenotype is enhanced, causing most cells to use glutamine for anaplerosis. Surprisingly, it has been found that resistance to glutamine inhibitor therapy is correlated to the expression of a cystine/glutamate transporter, SLC7A11 (also referred to as xCT), in the cancer cell. When the SLC7A11 is expressed in the cancer cell, the cancer cell is sensitive to glutaminase inhibitor therapy. Based on this finding, patients that are sensitive to glutaminase inhibitor therapy may now be identified in advance of treatment, saving patients who are resistant to therapy needless clinical intervention.

In addition to the analytical benefits achieved by being able to screen for patients who may be sensitive to the therapy, therapeutic methods for sensitizing a resistant cancer cell to glutaminase inhibitor therapy have also been developed. It has been discovered, quite surprisingly, that altering levels of cystine in a cancer cell microenvironment causes the cancer cells to become sensitive to glutaminase inhibitor therapy. Levels of cystine in the microenvironment can be influenced, for instance, by administering exogenous cystine (cystine or cysteine) to a subject having cancer and/or inducing expression of SLC7A11 in a cancer cell in vivo. These therapies sensitize the cancer cell, allowing the subject to respond to glutaminase inhibitor therapy. Additionally even if a subject is sensitive to glutaminase inhibitor therapy, the subject may benefit from the administration of cystine or SLC7A11 inducers. These therapies may enhance the sensitivity to glutaminase inhibitor therapy further and/or prevent the cancer cells from developing resistance to the therapy.

Thus, in some aspects, the invention is a composition of a glutaminase inhibitor and cystine in a pharmaceutically acceptable carrier. Cystine is the di-sulfide bond dimer of two cysteines. Cystine is the form of cysteine that circulates in the blood. The invention describes the administration of cystine to a subject having cancer. As used herein, the term "cystine" when administered to a subject, is used to encompass both cystine (the dimer) and cysteine (the monomer) and derivatives and prodrugs thereof. The administration of either cysteine or cystine will result in an increased level of circulating cystine, leading to the therapeutic treatment of the subject. Thus, in some embodiments the cystine is L-cysteine and in other embodiments the cystine is L-cystine. In some embodiments cystine is a mixture of the two.

The cystine may be formulated such that it will produce a 50-300 micromolar concentration in blood of the subject. In other embodiments the cystine is formulated to produce a 100-150 micromolar concentration in blood of the subject. For instance the cystine may be present in the composition in an amount sufficient to produce a concentration of greater than 0.5 mmol/kg.

In some embodiments, the cystine is administered to the subject in the form of a nutritional supplement of cystine or cysteine. Nutritional supplements are commercially available.

Cystine includes cystine derivatives such as the salt form of cystine and cysteine. Other cystine derivatives include but are not limited to glutathione, glutathione disulfide (oxidized glutathione), glutathione alkyl ester (e.g., glutathione ethyl ester etc.), oxidized glutathione dialkyl ester (e.g., oxidized glutathione diethyl ester etc.) and the like.

A cystine prodrug, as used herein refers to a drug which increases the level of cystine when administered to a subject. Cystine prodrugs include but are not limited to N-acetylcysteme ("NAC"), cysteine alkyl ester (e.g., cysteine methyl ester, cysteine ethyl ester etc.), 3-[(carboxymethyl)thio]alanine, N-acylcysteine (e.g., N-acetylcysteine etc.), N-acylcysteine alkyl ester (e.g., N-acetylcysteine methyl ester, N-acetylcysteine ethyl ester etc.), N-acylcystine (e.g., N-acetylcystine etc.), N-acylcystine alkyl ester (e.g., N-acetylcystine methyl ester etc.), N,N'-diacylcystine (e.g., N,N'-diacetylcystine etc.), N,N'-diacylcystine dialkyl ester (e.g., N,N'-diacetylcystine dimethyl ester, N,N'-diacetylcystine diethyl ester etc.), S-alkylcysteine sulfoxide and the structures described in US Patent Application 2015/0175559, incorporated by reference for the disclosure of cystine prodrugs.

Glutaminase inhibitors are known in the art and include for instance small molecule glutaminase inhibitors, such as BPTES (bis-2-[5-(phenylacetamido)-1,3,4-thiadiazol-2-yl] ethyl sulfide), DON (6-diazo-5-oxo-L-norleucine), and CB-839 (Calithera Bioscience, San Francisco, Calif.) as well as pharmaceutically acceptable salt thereof. BPTES analogs are also described in USP 20170209387.

In certain embodiments, the glutaminase inhibitor is a compound of formula I,

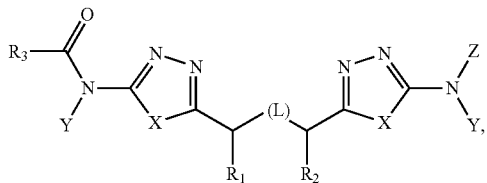

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH=CH$, or

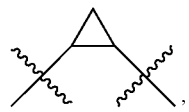 [SMILES: *C1CC1*]

wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy; X, independently for each occurrence, represents S, O or CH=CH, preferably S or CH=CH, wherein any hydrogen atom of a CH unit may be replaced by alkyl; Y, independently for each occurrence, represents H or $CH_2O$ (CO)$R_7$; $R_7$, independently for each occurrence, represents H or substituted or unsubstituted alkyl, alkoxy, aminoalkyl, alkylaminoalkyl, heterocyclylalkyl, arylalkyl, or heterocyclylalkoxy; Z represents H or $R_3$(CO); $R_1$ and $R_2$ each independently represent H, alkyl, alkoxy or hydroxy; $R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$; $R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; $R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments of the methods described herein, the glutaminase inhibitor is a compound of formula Ia,

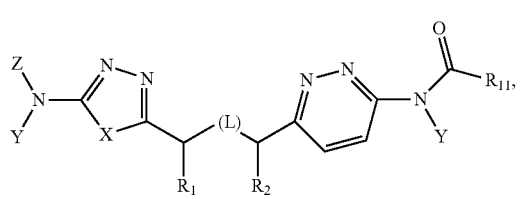

or a pharmaceutically acceptable salt thereof, wherein: L is as described above, preferably CH$_2$CH$_2$, wherein any hydrogen atom of a CH or CH$_2$ unit may be replaced by alkyl or alkoxy, any hydrogen of an NH unit may be replaced by alkyl, and any hydrogen atom of a CH$_2$ unit of CH$_2$CH$_2$, CH$_2$CH$_2$CH$_2$ or CH$_2$ may be replaced by hydroxy; X represents S, O or CH=CH, preferably S or CH=CH, wherein any hydrogen atom of a CH unit may be replaced by alkyl; Y, independently for each occurrence, represents H or CH$_2$O (CO)R$_7$; R$_7$, independently for each occurrence, represents H or substituted or unsubstituted alkyl, alkoxy, aminoalkyl, alkylaminoalkyl, heterocyclylalkyl, arylalkyl, or heterocyclylalkoxy; Z represents H or R$_3$(CO); R$_1$ and R$_2$ each independently represent H, alkyl, alkoxy or hydroxy, preferably H; R$_3$ represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or C(R$_8$)(R$_9$)(R$_{10}$), N(R$_4$)(R$_5$) or OR$_6$, wherein any free hydroxyl group may be acylated to form C(O)R$_7$; R$_4$ and R$_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$; R$_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$; and R$_8$, R$_9$ and R$_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or R$_8$ and R$_9$ together with the carbon to which they are attached, form a carbocyclic or heterocyclic ring system, wherein any free hydroxyl group may be acylated to form C(O)R$_7$, and wherein at least two of R$_8$, R$_9$ and R$_{10}$ are not H; R$_{11}$ represents substituted or unsubstituted aryl, arylalkyl, aryloxy, aryloxyalkyl, heteroaryl, heteroarylalkyl, heteroaryloxy, or heteroaryloxyalkyl, or C(R$_{12}$)(R$_{13}$)(R$_{14}$), N(R$_4$)(R$_{14}$) or OR$_{14}$, wherein any free hydroxyl group may be acylated to form C(O)R$_7$; R$_{12}$ and R$_{13}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R$_7$, and wherein both of R$_{12}$ and R$_{13}$ are not H; and R$_{14}$ represents substituted or unsubstituted aryl, arylalkyl, aryloxy, aryloxyalkyl, heteroaryl, heteroarylalkyl, heteroaryloxy, or heteroaryloxyalkyl.

In certain embodiments of the methods described herein, the glutaminase inhibitor is a compound having the structure of Formula (II):

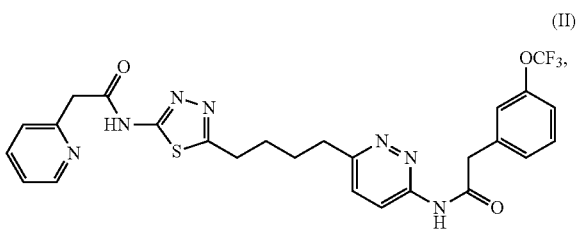 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof.

In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

In certain embodiments, the glutaminase inhibitor is selected from any one of the compounds disclosed in Table 3 of PCT Application Publication Number WO 2013/078123, published May 30, 2013, the contents of which are incorporated herein by reference.

In certain embodiments, the glutaminase inhibitor may be a prodrug of a compound of formula I or Ia, e.g., wherein a hydroxyl in the parent compound is presented as an ester or a carbonate, or carboxylic acid present in the parent compound is presented as an ester. In other embodiments, the glutaminase inhibitor may be racemic. In certain embodiments, glutaminase inhibitor compounds may be enriched in one enantiomer. In certain such embodiments, the inhibitors may be enriched in one or more diastereomer.

A subject having cancer may be administered a glutaminase inhibitor and cystine in an effective amount to treat the subject. The glutaminase inhibitor and cystine may be administered together in a single formulation. As such the compounds may be admixed in varying amounts depending on the subject or type of cancer to be treated. In other embodiments the glutaminase inhibitor and cystine may be administered in separate formulations. The two compositions may be administered at the same time but in separate formulations. Alternatively the cystine may be administered before or after the glutaminase inhibitor. The time between the administration of the glutaminase inhibitor and cystine may be, for instance, 5 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 36 hours 48 hours, 3 days, 4 days, 5 days, 6 days, 7 days, 2 weeks, 3 weeks or 1 month apart or any time frame in between.

In some instances, the glutaminase inhibitor and cysteine are co-administered such that the second of the two compounds administered is administered while the first compound is still effective in the body (e.g., the two compounds are simultaneously effective in the patient, which may include and additive or synergistic effects of the two compounds). When the interaction causes an increase in the effects of one or both of the drugs the interaction, the degree to which the final effect of the combined drugs is greater than administering either drug alone can be calculated resulting in what is called the "combination index" (CI). A combination index at or around 1 is considered "additive"; whereas a value greater than 1 is considered "synergistic".

In some embodiments the subject may be administered multiple doses of cystine. In other embodiments the subject may be administered multiple doses of glutaminase inhibitors. In yet other embodiments the subject may be administered multiple doses of both cystine and glutaminase inhibitors. In some embodiments the subject is administered 2, 3, 4, 5, 6, 7, 8, 9, 10, 11, 12, 13, 14, 15, 16, 17, 18, 19, 20, 21, 22, 23, 24, 25, 26, 27, 28, 29 or 30 doses of glutaminase inhibitors and/or cystine.

The methods of the invention are useful in some aspects for enhancing a glutaminase inhibitor therapy by determining whether the subject is sensitive to the therapy, by measuring SLC7A11. SCL7A11 is a member of a heteromeric, sodium-independent, anionic amino acid transport system that is highly specific for cysteine and glutamate. In this system, designated xCT, or CCBR1 the anionic form of cysteine is transported in exchange for glutamate. The UniProtKB/Swiss-Prot for SLC7A11 gene is XCT_HUMAN, Q9UPY5. The Gene ID for SLC7A11 is 23657.

The methods of the invention are useful in some aspects for enhancing a glutaminase inhibitor therapy in a subject using a SLC7A11 inducer. The subject receiving glutaminase inhibitor therapy is administered a SLC7A11 inducer in an effective amount to induce expression of SLC7A11 in a cancer cell of the subject, thereby sensitizing the subject to the glutaminase inhibitor therapy. An SLC7A11 inducer, as used herein, is a compound that causes an increase in expression level of a cystine/glutamate transporter, referred to as SLC7A11, in a cancer cell. The increase may be measured relative to the level of expression in a cancer cell of the subject prior to the treatment or relevant to a known normal level for a particular cancer cell.

The SLC7A11 inducer may be, for instance, a small molecule Nrf2 activator (such as those disclosed in US Published Patent Application 20160318917, incorporated by reference), KI-696 (inhibitor of KEAP1-NRF2 protein-protein interaction), dimethyl fumarate (commercially available for instance as Fumaderm or Tecfidera), Synthetic triterpenoids such as Bardoxolone methyl (CDDO-Me), 2-fluoro-4-(methoxycarbonyl)phenylboronic acid (AI-3), a miRNA, VEDA-1209 (Cureveda LLC), or nucleic acid encoding SLC7A11, such as a DNA or an mRNA encoding SLC7A11.

The invention also includes methods for detecting the presence or absence of a cystine/glutamate transporter in a cancer cell. These methods involve (a) obtaining a cancer cell from a human subject; and (b) detecting whether a cystine/glutamate transporter, SLC7A11, is expressed in the cancer cell, wherein if the SLC7A11 is expressed in the cancer cell, the cancer cell is sensitive to glutaminase inhibitor therapy. Measurement of SLC7A11 may be achieved using known methods in the art. For instance the expression level of SLC7A11 may be determined using positron emission tomography (PET) imaging. Commercially available reagents such as $^{18}$F-propyl-glutamate may be used in the PET imaging. Other medical imaging techniques include magnetic resonance imaging (MRI) and computed tomography (CT). PET is a fairly advanced clinical imaging technique in the field of nuclear medicine. Functional information relating to metabolic activities may be obtained by way of detectable gamma rays to diagnose a disease.

The expression levels of SLC7A11 are measured in a body in vivo or in an isolated sample. In some embodiments, expression products are mRNAs corresponding to the SLC7A11. In some embodiments, detecting the levels of expression products comprises exposing the sample to nucleic acid probes complementary to the mRNAs corresponding to the SLC7A11. In some embodiments, nucleic acid probes are covalently linked to a solid surface. In some embodiments, detecting the levels of expression products comprises use of a detection technique selected from the group consisting of microarray analysis, reverse transcriptase PCR, quantitative reverse transcriptase PCR, digital PCR and hybridization analysis.

In some embodiments, detection of expression products comprises generation of cDNA (e.g., by reverse transcription) from the mRNA (e.g., SLC7A11mRNA) in a sample, and detecting the cDNA. In some embodiments, cDNA is further amplified prior to detection (e.g., by qPCR). In some embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA may be detected or used as a template for a PCR reaction. PCR products can be detected by any suitable method, including but not limited to, gel electrophoresis and staining with a DNA specific stain or hybridization to a labeled probe.

In some embodiments, expression products are proteins corresponding to the SLC7A11. In some embodiments, detecting the levels of expression products comprises exposing the sample to antibodies (or antibody fragments, or aptamers, etc.) for the proteins corresponding to the SLC7A11. In some embodiments, antibodies are covalently linked to a solid surface. In some embodiments, detecting the levels of expression products comprises exposing the sample to a mass analysis technique (e.g., mass spectrometry).

As used herein, the term "sample" is used in its broadest sense. In one sense it can refer to biological samples obtained from animals (including humans) and encompass fluids, solids, tissues (e.g., neurological tissue), and gases. Biological samples include blood products (e.g., plasma and serum), saliva, urine.

The terms "specific binding" or "specifically binding" when used in reference to the interaction of capture or detection reagent (e.g., antibody probe etc.) and a target (e.g., protein, DNA, RNA, etc.) means that the interaction is dependent upon the presence of a particular structure (i.e., the nucleic acid sequence).

As used herein, the terms "non-specific binding" and "background binding" when used in reference to the interaction capture or detection reagent (e.g., antibody probe etc.) and a target (e.g., protein, DNA, RNA, etc.) refer to an interaction that is not dependent on the presence of a particular structure or sequence.

As used herein, "a reagent that specifically detects expression levels" refers to reagents used to detect the expression of SLC7A11. Examples of suitable reagents include but are not limited to, nucleic acid probes capable of specifically hybridizing to the SLC7A11, aptamers, PCR primers capable of specifically amplifying the SLC7A11, and antibodies capable of specifically binding to proteins expressed by the SLC7A11.

As used herein, the term "nucleic acid detection assay" refers to any method of determining the nucleotide composition of a nucleic acid of interest. Nucleic acid detection assay include but are not limited to, DNA sequencing methods, probe hybridization methods, enzyme mismatch cleavage methods; polymerase chain reaction; branched hybridization methods; rolling circle replication; NASBA; molecular beacon technology; E-sensor technology; cycling probe technology; Dade Behring signal amplification methods; ligase chain reaction; and sandwich hybridization methods.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition.

The level of SLC7A11 present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; a threshold value; an acceptable range; etc.

In some embodiments, the SLC7A11 is detected at the nucleic acid (e.g., RNA) level. For example, the amount of SLC7A11 RNA (e.g., mRNA) present in a sample is determined (e.g., to determine the level of SLC7A11 expression). SLC7A11 nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, and nucleic acid amplification.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction, commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. In some embodiments, PCR is digital PCR.

Non-amplified or amplified nucleic acids can be detected by any conventional means. For example, in some embodiments, nucleic acids are detected by hybridization with a detectably labeled probe and measurement of the resulting hybrids.

In some embodiments, the present invention provides a method of treating a cancer comprising administering to a subject in whom such treatment is desired a therapeutically effective amount of a composition comprising a cystine or SLC7A11 inducer. A composition of the invention may, for example, be used as a first, second, third or fourth line cancer treatment. In some embodiments, the invention provides methods for treating a cancer (including ameliorating a symptom thereof) in a subject refractory to conventional glutaminase inhibitor therapies for such a cancer, said methods comprising administering to said subject a therapeutically effective amount of a composition comprising a cystine or SLC7A11 inducer. A cancer may be determined to be refractory to a therapy when at least some significant portion of the cancer cells are not killed or their cell division are not arrested in response to the glutaminase inhibitor therapy. Such a determination can be made either in vivo or in vitro by any method known in the art for assaying the effectiveness of treatment on cancer cells, using the art-accepted meanings of "refractory" in such a context. In alternative embodiments the cancer cell may be determined to by refractory or resistant when the expression level of SLC7A11 is low. In a specific embodiment, a cancer is refractory where the number of cancer cells has not been significantly reduced, or has increased.

In some embodiments of the methods described herein the cancer is non-small cell lung cancer (NSCLC). There are several subtypes of NSCLC, including squamous cell lung carcinoma, adenocarcinoma and large cell lung carcinoma. Typical treatment of NSCLC involves surgery; however, only a quarter of the patients undergo successful resection, with a recurrence rate of 50%. Therapeutic approaches in advanced disease involve chemotherapy and/or radiotherapy. One of the chemotherapeutic approaches used today are combinations of platin-based substances with e.g. Gemcitabin. Another type of therapy used for the treatment of NSCLC is the Targeted Therapy which attempts to influence tumor specific target structures on a molecular level. Substances used include Bevacizumab (an angiogenesis inhibitor) or Erlotinib, which is aimed at the tyrosine kinases of the epidermal growth factor receptor (EGFR). The compositions and methods of the invention may be used alone or in combination with any of these therapies for the treatment of NSCLC.

The invention also provides methods for treating cancer by administering the compositions described herein in combination with any other anti-cancer treatment (e.g., radiation therapy, chemotherapy or surgery). The invention also provides alternative methods for the treatment of cancer where chemotherapy, radiation therapy, hormonal therapy, and/or biological therapy/immunotherapy has proven or may prove too toxic, i.e., results in unacceptable or unbearable side effects, for the subject being treated.

Cancers that can be treated by the methods encompassed by the invention include, but are not limited to, neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below to the extent such cancers are responsive to glutaminase inhibitor therapy.

Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

The compositions of the invention also can be administered to prevent progression to a neoplastic or malignant state. Such prophylactic use is indicated in conditions known or suspected of preceding progression to neoplasia or cancer, in particular, where non-neoplastic cell growth consisting of hyperplasia, metaplasia, or most particularly, dysplasia has occurred. Hyperplasia is a form of controlled cell proliferation involving an increase in cell number in a tissue or organ, without significant alteration in structure or function. Endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

In one embodiment, the methods of the invention can be used in conjunction with one or more other forms of cancer treatment, for example, in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. Any agent or therapy (e.g., chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein. One of ordinary skill in the medical arts can determine an appropriate treatment for a subject.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand-breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the nonintercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colcbicine, Vincristine and Vinblastine, both alkaloids and Paclitaxel and cytoxan; hormonal agents including, but note limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, antiandrogen agents such as Flutamide; and antiadrenal agents such as Mitotane and Aminoglutethimide; cytokines including, but not limited to, IL-1.alpha., IL-1β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β, IFN-γ, and Uteroglobins (U.S. Pat. No. 5,696,092); anti-angiogenics including, but not limited to, agents that inhibit VEGF (e.g., other neutralizing antibodies (Kim et al., 1992; Presta et al., 1997; Sioussat et al., 1993; Kondo et al., 1993; Asano et al., 1995, U.S. Pat. No. 5,520,914), soluble receptor constructs (Kendall and Thomas, 1993; Aiello et al., 1995; Lin et al., 1998; Millauer et al., 1996), tyrosine kinase inhibitors (Siemeister et al., 1998, U.S. Pat. Nos. 5,639,757, and 5,792,771), antisense strategies, RNA aptamers and ribozymes against VEGF or VEGF receptors (Saleh et al., 1996; Cheng et al., 1996; Ke et al., 1998; Parry et al., 1999); variants of VEGF with antagonistic properties as described in WO 98/16551; compounds of other chemical classes, e.g., steroids such as the angiostatic 4,9(11)-steroids and C21-oxygenated steroids, as described in U.S. Pat. No. 5,972,922; thalidomide and related compounds, precursors, analogs, metabolites and hydrolysis products, as described in U.S. Pat. Nos. 5,712,291 and 5,593,990; Thrombospondin (TSP-1) and platelet factor 4 (PF4); interferons and metalloproteinsase inhibitors; tissue inhibitors of metalloproteinases (TIMPs); anti-Invasive Factor, retinoic acids and paclitaxel (U.S. Pat. No. 5,716,981); AGM-1470 (Ingber et al., 1990); shark cartilage extract (U.S. Pat. No. 5,618,925); anionic polyamide or polyurea oligomers (U.S. Pat. No. 5,593,664); oxindole derivatives (U.S. Pat. No. 5,576,330); estradiol derivatives (U.S. Pat. No. 5,504,074); thiazolopyrimidine derivatives (U.S. Pat. No. 5,599,813); and LM609 (U.S. Pat. No. 5,753,230); apoptosis-inducing agents including, but not limited to, bcr-abl, bcl-2 (distinct from bcl-1, cyclin D1; GenBank accession numbers M14745, X06487; U.S. Pat. Nos. 5,650,491; and 5,539,094) and family members including Bcl-x1, Mcl-1, Bak, A1, A20, and antisense nucleotide sequences (U.S. Pat. Nos. 5,650,491; 5,539,094; and 5,583,034); Immunotoxins and coaguligands, tumor vaccines, and antibodies.

Other anti-cancer drugs include, but are not limited to: 20-epi-1,25 dihydroxyvitamin D3; 5-ethynyluracil; angiogenesis inhibitors; anti-dorsalizing morphogenetic protein-1; ara-CDP-DL-PTBA; BCR/ABL antagonists; CaRest M3; CARN 700; casein kinase inhibitors (ICOS); clotrimazole; collismycin A; collismycin B; combretastatin A4; crambescidin 816; cryptophycin 8; curacin A; dehydrodidemnin B; didemnin B; dihydrotaxol, duocarmycin SA; kahalalide F; lamellarin-N triacetate; leuprolide+estrogen+progesterone; lissoclinamide 7; monophosphoryl lipid A+myobacterium cell wall sk; N-acetyldinaline; N-substituted benzamides; 06-benzylguanine; placetin A; placetin B; platinum complex; platinum compounds; platinum-triamine complex; rhenium Re 186 etidronate; RII retinamide; rubiginone B 1; SarCNU; sarcophytol A; sargramostim; senescence derived inhibitor 1; spicamycin D; tallimustine; 5-fluorouracil; thrombopoietin; thymotrinan; thyroid stimulating hormone; variolin B; thalidomide; velaresol; veramine; verdins; verteporfin; vinorelbine; vinxaltine; vitaxin; zanoterone; zeniplatin; and zilascorb.

The compounds described herein may be formulated as pharmaceutical compositions with pharmaceutically acceptable carriers. The compounds are administered to the subject in an effective amount for treating cancer. An "effective amount", for instance, is an amount necessary or sufficient to realize a desired biologic effect. An "effective amount for treating cancer, for instance, could be that amount necessary to (i) prevent or slow further growth of a cancer and/or (ii) kill existing cancer cells. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of the cancer. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 μg to 10,000 mg, more typically from about 1 μg/day to 8000 mg, and most typically from about 10 μg to 100 μg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Pharmaceutical compositions of the present invention comprise an effective amount of one or more agents, dissolved or dispersed in a pharmaceutically acceptable carrier.

The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be nontoxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition of the invention can be used directly or can be mixed with suitable adjuvants and/or carriers. Suitable adjuvants include aluminum salt adjuvants, such as aluminum phosphate or aluminum hydroxide, calcium phosphate nanoparticles (BioSante Pharmaceuticals, Inc.), ZADAXIN™, nucleotides ppGpp and pppGpp, killed *Bordetella pertussis* or its components, *Corenybacterium* derived P40 component, cholera toxin and mycobacteria whole or parts, and ISCOMs (DeVries et al., 1988; Morein et al., 199&, Lovgren: al., 1991). The skilled artisan is familiar with carriers appropriate for pharmaceutical use or suitable for use in humans.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). WO 95/24929 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases or recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is a cystine or SCL7A11 inducer and a pharmaceutically acceptable carrier, and said instructions indicate a dosing regimen for treating a subject with cancer. In another embodiment, an article of manufacture comprises packaging material and a pharmaceutical agent and instructions contained within said packaging material. In another embodiment, an article of manufacture comprises packaging material and two pharmaceutical agents and instructions contained within said packaging material, wherein said first pharmaceutical agent is a cystine or SCL7A11 inducer and a pharmaceutically acceptable carrier, and said second pharmaceutical agent is a therapeutic agent other than a cystine or SCL7A11 inducer and said instructions indicate a dosing regimen for preventing, treating or managing a subject with a cancer.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The following experiments were performed in accordance with the invention. The present invention is further illustrated by these experiments, which in no way should be construed as further limiting.

Materials and Methods:

Cell lines growing in log phase in RPMI medium were trypsinized, counted and plated into 6 well dishes in 2 mL of RPMI medium and incubated overnight. Initial seeding density was 20,000 cells/well for A549 cells, or 50,000 cells for MCF7, AU565 and MDA-MB-468 cells. The next day, a plate of cells was trypsinized and counted to provide a number of cells at the start of the experiment. Cells were then washed twice with 2 mL of PBS, and 8 mL of the indicated media premixed with indicated compounds or vehicles was added. Cells were then counted 4 days after adding the indicated medias. Proliferation rate was determined using the following formula:

Proliferation rate in doublings/day=[Log 2(Final Day 4 cell count/Initial Day 0 cell count)]/4 days. Cells were counted using a Cellometer Auto t$ Plus Cell Counter (Nexcelom Bioscience).

Example 1

An interesting question is why cancer cells require glutamine if not for protein and as a nitrogen donor. For many cells, the carbon skeleton is used for anaplerosis, and contributes to the formation of metabolites. Glutamine can enter the TCA cycle, and glutaminase is an enzyme that allows the entry of glutamine carbon into the TCA cycle. Of note, aspartate may be one important product of glutamine anaplerosis, and aspartate levels drop dramatically with glutamine withdrawal in lung cancer cells. The addition of aspartate alone allows these cells to proliferate in the absence of glutamine. As many cancer cells require glutamine entry into the TCA cycle to proliferate in vitro, and this depends on glutaminase, this has led to the development of clinical glutaminase inhibitors.

Also of interest is what drives cancer cell glutamine anaplerosis. Not all cancer cells lines require extracellular glutamine to proliferate, and a number of studies have sought to understand the genetic and molecular basis of glutamine "addiction" in comparison to glutamine "independent" cells. Glutamine dependency is thought to be at least in part oncogenotype-dependent, with MYC and RAS oncogenes both being thought to drive glutamine addiction. However, the exact genetic basis for glutamine addiction remains unknown, and is pressing to understand because it will be essential for identifying patients that would benefit from clinical glutaminase inhibitors.

Beyond oncogenotype, the environment of the tumor cell can determine its dependency of glutaminase for anaplerosis and proliferation. RAS NSCLC in vivo do not label the TCA cycle with glutamine, whereas in vitro these cell lines do. This distinction correlates with glutaminase inhibitor sensitivity.

Quite surprisingly, the inventors have identified an environmental factor in vivo that suppress glutamine anaplerosis, and that in tissue culture models enhance this metabolic phenotype. Such factors were sought to be isolated: to have a better, more representative and predictive tissue culture model, and to understand and potentially overcome cell line resistance to clinical glutaminase inhibitor that tumors have in vivo.

The studies according to the invention have identified the factor(s) contributing to differential glutamine anaplerosis between human NSCLC tumors growing in vivo and cell lines cultured in vitro. A variable that is significantly different for cancer cells growing as tumors in vivo and in vitro is nutrient availability. To address the possibility that environmental nutrient levels affect glutamine anaplerosis and dependency, the human NSCLC cell line A549 was grown in a medium that more closely models in vivo nutrient levels, adult bovine serum. The glutamine contribution to the TCA cycle was measured using stable isotope tracers and glutaminase inhibitor sensitivity and the growth in adult bovine serum was observed to decrease glutamine anaplerosis to levels seen for A549 tumors growing in vivo. It was found that difference in levels of a single nutrient between adult bovine serum and standard tissue culture media, cystine, largely dictates the observed difference in glutamine anaplerosis, and does so via the cystine/glutamate antiporter xCT/SLC7A11. Lastly, it was found that administration of cystine to tumor bearing mice, increases tumor glutamine anaplerosis in vivo. Collectively, the results suggest that environmental cystine availability and xCT expression, are critical determinants of glutamine anaplerosis and glutaminase dependency. These results identify new markers of glutamine dependence, suggesting a way to potentiate clinical glutaminase inhibitors, and highlighting the importance of accurately modeling nutrient conditions for in vitro studies.

Example 2

TABLE 1

Amino acid, glucose, pyruvate and lactate concentrations in all medias used in this study compared to human plasma clinical reference values

| Metabolite | Human male plasma reference range$^a$ [μM] | RPMI-1640 with 10% dialyzed fetal bovine serum [μM] | DMEM with 10% dialyzed fetal bovine serum [μM] | Adult bovine serum$^b$ [μM] | Adult bovine heparinized plasma$^b$ [μM] | Adult human serum$^b$ [μM] |
|---|---|---|---|---|---|---|
| Alanine | 146-494 | 0 | 0 | 314 +/− 6 | 321 +/− 3 | 670 +/− 13 |
| Arginine | 28-96 | 1034 | 360 | 312 +/− 10 | 150 +/− 9 | 216 +/− 8 |
| Aspargine | 32-92 | 341 | 0 | 17 +/− 1 | 19 +/− 1 | 81 +/− 2 |
| Aspartate | 2-9 | 135 | 0 | 7.4 +/− 0.4 | 5.3 +/− 0.4 | 59.2 +/− 1.3 |
| Cystine | 24-54 | 187 | 180 | 0.3 +/− 0.1 | 2 +/− 0.1 | 3.4 +/− 0.2 |
| Glutamate | 6-62 | 122 | 0 | 192 +/− 3 | 120 +/− 1 | 348 +/− 5 |
| Glutamine | 466-798 | 1849 | 3600 | 183 +/− 4 | 291 +/− 1 | 409 +/− 7 |
| Glycine | 147-299 | 1200 | 360 | 302 +/− 6 | 221 +/− 1 | 409 +/− 8 |
| Histidine | 72-108 | 87 | 180 | 8.9 +/− 0.2 | 8.2 +/− 0.2 | 17.7 +/− 0.3 |
| Isoleucine | 46-90 | 344 | 720 | 112 +/− 2 | 84 +/− 1 | 114 +/− 1 |
| Leucine | 113-205 | 344 | 720 | 218 +/− 3 | 172 +/− 1 | 231 +/− 5 |
| Lysine | 135-243 | 197 | 720 | 92 +/− 2 | 146 +/− 1 | 206 +/− 4 |
| Methionine | 13-37 | 91 | 180 | 21 +/− 1 | 26 +/− 1 | 39 +/− 1 |
| Phenylalanine | 46-74 | 82 | 360 | 92 +/− 2 | 68 +/− 1 | 144 +/− 3 |
| Proline | 97-297 | 157 | 0 | 88 +/− 2 | 61 +/− 1 | 301 +/− 4 |
| Serine | 89-165 | 257 | 360 | 119 +/− 2 | 74 +/− 1 | 237 +/− 5 |

TABLE 1-continued

Amino acid, glucose, pyruvate and lactate concentrations in all medias used in this study compared to human plasma clinical reference values

| Metabolite | Human male plasma reference range[a] [μM] | RPMI-1640 with 10% dialyzed fetal bovine serum [μM] | DMEM with 10% dialyzed fetal bovine serum [μM] | Adult bovine serum[b] [μM] | Adult bovine heparinized plasma[b] [μM] | Adult human serum[b] [μM] |
|---|---|---|---|---|---|---|
| Threonine | 92-180 | 151 | 720 | 63 +/− 1 | 50 +/− 1 | 192 +/− 3 |
| Tryptophan | 25-65 | 22 | 72 | ND | ND | ND |
| Tyrosine | 37-77 | 99 | 360 | 56 +/− 1 | 47 +/− 1 | 101 +/− 3 |
| Valine | 179-335 | 154 | 720 | 251 +/− 5 | 181 +/− 2 | 325 +/− 6 |
| Glucose | | 9990 | 22500 | 3932 +/− 26 | 8403 +/− 33 | 2407 +/− 23 |
| Pyruvate | 27-160 | 0 | 900 | 9.4 +/− 0.2 | 70.8 +/− 0.5 | 10.3 +/− 0.7 |
| Lactate | | 0 | 0 | 10878 +/− 217 | 9291 +/− 61 | 9250 +/− 178 |

[a]Shown is the range +/− 2 standard deviations from the mean value for the indicated metabolite.
These values are from [Blau et al].
[b]Shown are the mean values +/− the standard error of the mean for the indicated metabolites as determined by GC-MS, except glucose concentration, which was determined using a YSI bioanalyzer.
All samples were analyzed in triplicate.
ND indicates that the metabolite was not detected.

The entire contents of all of the references (including literature references, issued patents, published patent applications, and co-pending patent applications) cited throughout this application are hereby expressly incorporated by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating a subject, comprising administering to a subject having cancer a glutaminase inhibitor and cystine in an effective amount to treat the subject.

2. The method of claim 1, wherein the glutaminase inhibitor and cystine are administered together in a single formulation.

3. The method of claim 1, wherein the glutaminase inhibitor and cystine are administered in separate formulations.

4. The method of claim 1, wherein the cystine is administered before the glutaminase inhibitor.

5. The method of claim 1, wherein the cystine is L-cystine or L-cysteine.

6. The method of claim 1, wherein the cystine is administered to the subject as a cysteine formulation or as a cystine formulation.

7. The method of claim 1, wherein the cystine is administered in an amount to produce a 50-300 micromolar concentration in blood of the subject.

8. The method of claim 1, wherein the cystine is administered in an amount to produce a 100-150 micromolar concentration in blood of the subject.

9. The method of claim 1, wherein the cystine is administered in an amount greater than 0.5 mmol/kg.

10. The method of claim 1, further comprising determining whether a cystine/glutamate transporter, SLC7A11, is expressed in a cancer cell of the subject, wherein if the SLC7A11 is expressed in the cancer cell, the cancer cell is sensitive to glutaminase inhibitor therapy.

11. The method of claim 1, wherein the subject has low levels or no expression of SLC7A11.

12. The method of claim 1, wherein the subject has high levels of SLC7A11.

13. The method of claim 1, further comprising administering a SLC7A11 inducer to the subject.

14. A method for enhancing a glutaminase inhibitor therapy in a subject, comprising administering to a subject receiving glutaminase inhibitor therapy, cystine in an effective amount to sensitize the subject to the glutaminase inhibitor therapy.

15. The method of claim 14, wherein the cystine is administered in an amount to produce a 100-150 micromolar concentration in blood of the subject.

16. The method of claim 14, wherein the cystine is administered in an amount greater than 0.5 mmol/kg.

17. The method of claim 14, further comprising determining whether a cystine/glutamate transporter, SLC7A11, is expressed in a cancer cell of the subject, wherein if the SLC7A11 is expressed in the cancer cell, the cancer cell is sensitive to glutaminase inhibitor therapy.

18. The method of claim 1, wherein the cystine is L-cystine or L-cysteine.

19. A method for enhancing a glutaminase inhibitor therapy in a subject, comprising administering to a subject receiving glutaminase inhibitor therapy a SLC7A11 inducer in an effective amount to induce expression of SLC7A11 in a cancer cell of the subject, thereby sensitizing the subject to the glutaminase inhibitor therapy.

20. The method of claim 19, wherein the SLC7A11 inducer is a small molecule Nrf2 activator.

21. The method of claim 19, wherein the SLC7A11 inducer is KI-696.

22. The method of claim 19, wherein the SLC7A11 inducer is dimethyl fumarate.

23. The method of claim 19, wherein the SLC7A11 inducer is CDDO-Me.

24. The method of claim 19, wherein the SLC7A11 inducer is AI-3.

25. The method of claim 19, wherein the SLC7A11 inducer is a miRNA.

26. The method of claim 19, wherein the SLC7A11 inducer is VEDA-1209.

27. The method of claim 19, wherein the SLC7A11 inducer is a nucleic acid encoding SLC7A11.

28. The method of claim 19, further comprising administering cystine or cysteine to the subject.

29. The method of claim 19, further comprising determining whether SLC7A11 is expressed in a cancer cell of the subject, wherein if the SLC7A11 is expressed in the cancer cell, the cancer cell is sensitive to glutaminase inhibitor therapy.

30. A method for detecting the presence or absence of a cystine/glutamate transporter in a cancer cell, comprising:
 (a) obtaining a cancer cell from a human subject; and
 (b) detecting whether a cystine/glutamate transporter, SLC7A11, is expressed in the cancer cell, wherein if the SLC7A11 is expressed in the cancer cell, the cancer cell is sensitive to glutaminase inhibitor therapy,
 wherein the expression level of SLC7A11 is determined using PET imaging using a PET reagent, $^{18}$F-propyl-glutamate, and
 wherein the subject is administered cystine or cysteine in an effective amount to sensitize the subject to glutaminase inhibitor therapy.

31. The method of claim 30, further comprising administering to the subject an SLC7A11 inducer in an effective amount to sensitize the subject to glutaminase inhibitor therapy.

* * * * *